United States Patent
Cherukuri et al.

(10) Patent No.: US 6,344,222 B1
(45) Date of Patent: Feb. 5, 2002

(54) MEDICATED CHEWING GUM DELIVERY SYSTEM FOR NICOTINE

(75) Inventors: Subraman R. Cherukuri, Vienna, VA (US); John M. Pinney, Bethesda; Jack E. Henningfield, Baltimore, both of MD (US); Aradhana Sasan, Springfield, VA (US); Edward J. Cone, Severna Park, MD (US); Saul Shiffman, Pittsburgh, PA (US); Joe Gitchell, Chevy Chase; Carlos D. Malvestutto, Silver Spring, both of MD (US)

(73) Assignee: JSR LLC, Bethesda, MD (US)

( * ) Notice: Subject to any disclaimer, the term of this patent is extended or adjusted under 35 U.S.C. 154(b) by 0 days.

(21) Appl. No.: 09/389,339

(22) Filed: Sep. 2, 1999

Related U.S. Application Data

(63) Continuation-in-part of application No. 09/146,696, filed on Sep. 3, 1998.

(51) Int. Cl.⁷ .............................. A23G 3/30; A61K 9/68
(52) U.S. Cl. ............................ 426/6; 424/48; 424/440; 424/3
(58) Field of Search .......................... 426/3, 6; 424/48, 424/440, 441

(56) References Cited

U.S. PATENT DOCUMENTS

| | | | |
|---|---|---|---|
| 3,845,217 A | 10/1974 | Ferno et al. | 426/3 |
| 3,877,468 A | 4/1975 | Lichtneckert et al. | 131/2 |
| 3,901,248 A | 8/1975 | Lichtneckert et al. | 131/2 |
| 3,984,574 A | 10/1976 | Comollo | 426/4 |
| 4,163,777 A | 8/1979 | Mitra | 424/21 |
| 4,276,890 A | 7/1981 | Fichera | 131/270 |
| 4,311,691 A | 1/1982 | Fichera | 424/48 |
| 4,515,769 A | 5/1985 | Merritt et al. | 424/49 |
| 4,620,982 A | 11/1986 | Serpelloni | 426/658 |
| 4,639,368 A | 1/1987 | Niazi et al. | 424/48 |
| 4,671,953 A | 6/1987 | Stanley et al. | 424/440 |
| 4,711,784 A | 12/1987 | Yang | 426/5 |
| 4,806,356 A | 2/1989 | Shaw | 424/440 |
| 4,832,994 A | 5/1989 | Fey | 428/48 |
| 4,855,326 A | 8/1989 | Fuisz | 424/439 |
| 4,863,737 A | 9/1989 | Stanley et al. | 424/440 |
| 4,907,605 A | 3/1990 | Ray et al. | 131/270 |
| 4,963,369 A | 10/1990 | Song et al. | 426/5 |
| 4,967,773 A | 11/1990 | Shaw | 131/359 |
| 4,971,079 A | 11/1990 | Talapin et al. | 131/359 |
| 4,971,806 A | * 11/1990 | Cherukuri et al. | 426/3 |
| 4,983,378 A | 1/1991 | Parneu | 424/48 |
| 4,985,252 A | 1/1991 | Jung et al. | 424/439 |
| 5,069,904 A | 12/1991 | Masterson | 424/401 |
| 5,122,127 A | 6/1992 | Stanley | 604/890.1 |
| 5,132,114 A | 7/1992 | Stanley et al. | 424/440 |
| 5,135,753 A | 8/1992 | Baker et al. | 424/435 |
| 5,139,787 A | 8/1992 | Broderick et al. | 424/486 |
| 5,147,648 A | 9/1992 | Bannert | 424/435 |
| 5,147,654 A | 9/1992 | Place et al. | 424/473 |
| 5,154,927 A | 10/1992 | Song et al. | 424/440 |
| 5,154,939 A | 10/1992 | Broderick et al. | 426/5 |
| 5,158,772 A | 10/1992 | Davis | 424/401 |
| 5,198,251 A | 3/1993 | Sona et al. | 426/5 |

(List continued on next page.)

FOREIGN PATENT DOCUMENTS

| | | |
|---|---|---|
| CA | 2109895 | 5/1995 |
| GB | 2 255 892 | 11/1992 |
| GB | 2299756 | 10/1996 |
| WO | 9320821 | 10/1993 |
| WO | 9512399 | 5/1995 |
| WO | 9710162 | 3/1997 |
| WO | WO 97/42941 | 5/1997 |
| WO | 9741858 | 11/1997 |

OTHER PUBLICATIONS

"Chewing Gum as a Drug Delivery System", Margrethe Romer Rassing, Advanced Drug Delivery Rev., 1994.

"Drinking Coffee and Carbonated Beverages . . . ", Henningfield, et al, JAMA, Sep. 26, 1990—vol. 264, No. 12.

Nicotine Dependence, "Interface Between Tobacco and Tobacco Related Disease", Henningfield, pp. 37–55.

"Nicotine Gum: dose related effects on cigarette smoking and subjective ratings", Coslett, 1987.

"Drinking Coffee and Carbonated Beverages . . . ", Henningfield, pp. 1560–1564.

"Abuse Liability and Pharmacodynamic Characteristics of Intravenous . . . ", Henningfield, vol. 234, No. 1 pp. 1–12.

"Nicotine Gum: Chew Rate, Subjective Effects . . . ", Coslett, pp 747–751.

Primary Examiner—Arthur L. Corbin
(74) Attorney, Agent, or Firm—Liniak, Berenato, Longacre & White, LLC

(57) ABSTRACT

A chewing gum delivery system has nicotine, gum base and a buffer system with an improved release rate for the nicotine. The resulting delivery system advantageously provides a convenient, reliable, practical, and relatively painless system for delivering an active. The delivery system is capable of delivering initial and second doses of a craving reduction active or other actives (e.g., nicotine), the combination of which rapidly reduces cravings, or provides some other pharmacological effect, and provides the pharmacological effect or protection from such cravings over a prolonged period of time beyond the initial dose. Notably, the delivery system is capable of rapidly achieving a pharmacologically effective concentration of the active (e.g., nicotine) in the bloodstream (e.g., within 5 minutes, or more desirably within 3 minutes, or in some cases, within 1–2 minutes), and is also capable of keeping the concentration of the active in the bloodstream at or near the pharmacologically effective concentration for at least 20 minutes after chewing of the delivery system begins, or more desirably about 30 minutes to about 50 minutes after chewing begins.

21 Claims, 10 Drawing Sheets

U.S. PATENT DOCUMENTS

| | | | |
|---|---|---|---|
| 5,244,668 A | 9/1993 | Snipes | 424/435 |
| 5,288,497 A | 2/1994 | Stanley et al. | 424/440 |
| 5,288,498 A | 2/1994 | Stanley et al. | 424/440 |
| 5,302,394 A | 4/1994 | Beahm | 424/440 |
| 5,312,626 A | 5/1994 | Gergely et al. | 424/441 |
| 5,334,390 A | 8/1994 | Solomon et al. | 424/439 |
| 5,362,496 A | 11/1994 | Baker et al. | 424/435 |
| 5,364,627 A | 11/1994 | Song | 424/443 |
| 5,399,354 A | 3/1995 | Ells et al. | 424/440 |
| 5,437,872 A | 8/1995 | Lee | 424/464 |
| 5,462,754 A | 10/1995 | Synosky et al. | 426/4 |
| 5,487,902 A | 1/1996 | Anderson et al. | 426/3 |
| 5,488,962 A | 2/1996 | Perfetti | 131/270 |
| 5,525,351 A | 6/1996 | Dam | 424/440 |
| 5,543,424 A | 8/1996 | Carlsson et al. | 514/343 |
| 5,549,906 A | 8/1996 | Santus | 424/440 |
| 5,593,684 A | 1/1997 | Baker et al. | 424/435 |
| 5,599,554 A | 2/1997 | Majeti | 424/448 |
| 5,616,340 A | 4/1997 | Ells et al. | 424/440 |
| 5,662,920 A | 9/1997 | Santus | 424/435 |
| 5,721,257 A | 2/1998 | Baker et al. | 514/343 |
| 5,783,207 A | 7/1998 | Stanley et al. | 424/440 |
| 5,855,908 A | 1/1999 | Stanley et al. | 424/440 |
| 5,912,007 A | 6/1999 | Pan et al. | 424/440 |
| 5,935,604 A | 8/1999 | Illum | 424/501 |
| 5,955,098 A | 9/1999 | Dugger, III | 424/435 |
| 5,955,099 A | 9/1999 | White | 424/440 |
| 5,955,107 A | 9/1999 | Augello et al. | 424/465 |

\* cited by examiner

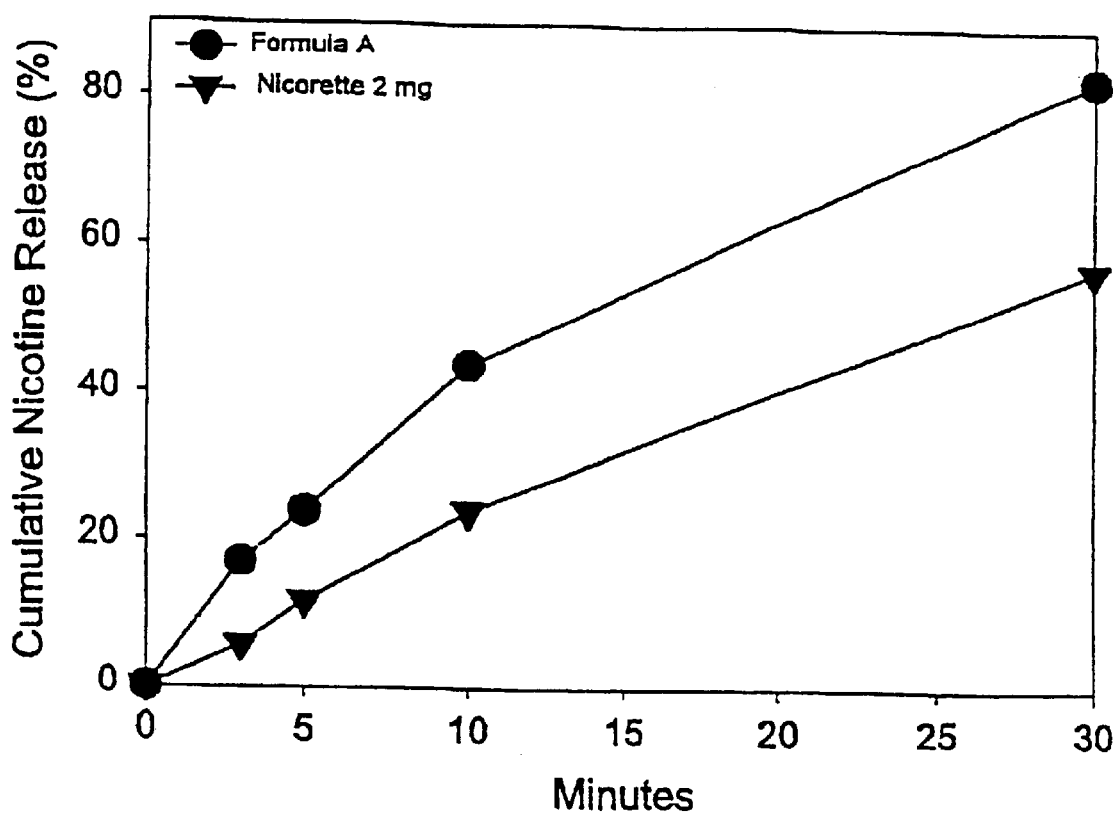
Figure 1A: Nicotine Release Profile Formula A vs. Nicorette 2mg

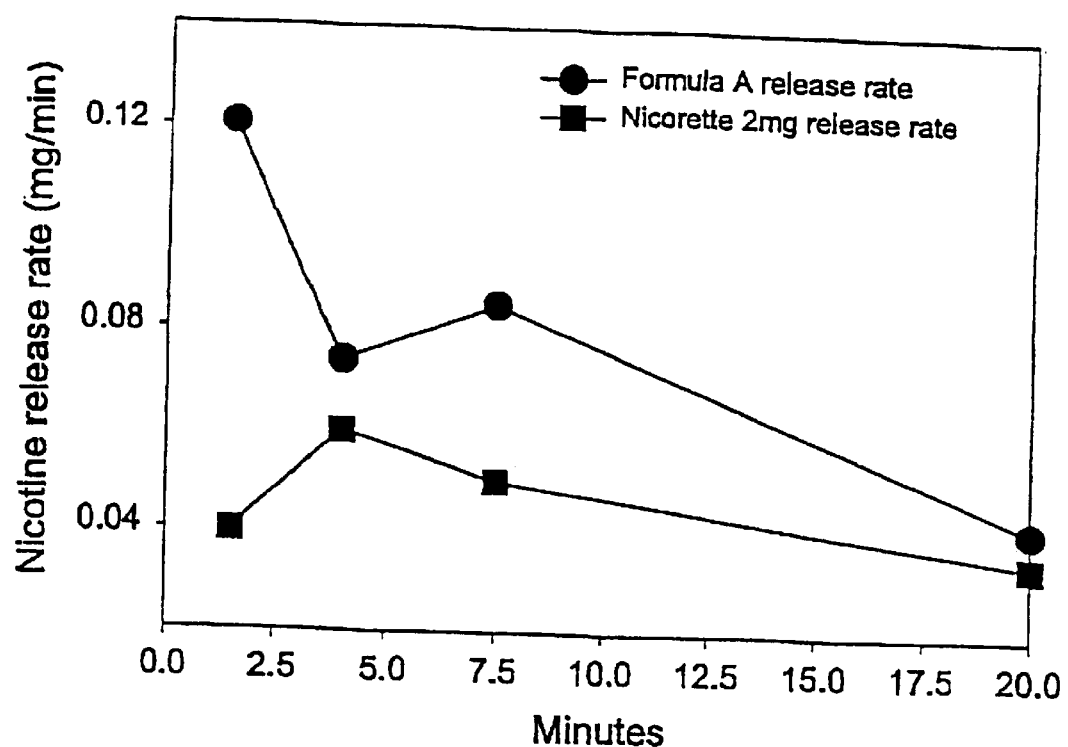
Figure 1B: Nicotine release rate for formula A vs. Nicorette 2mg

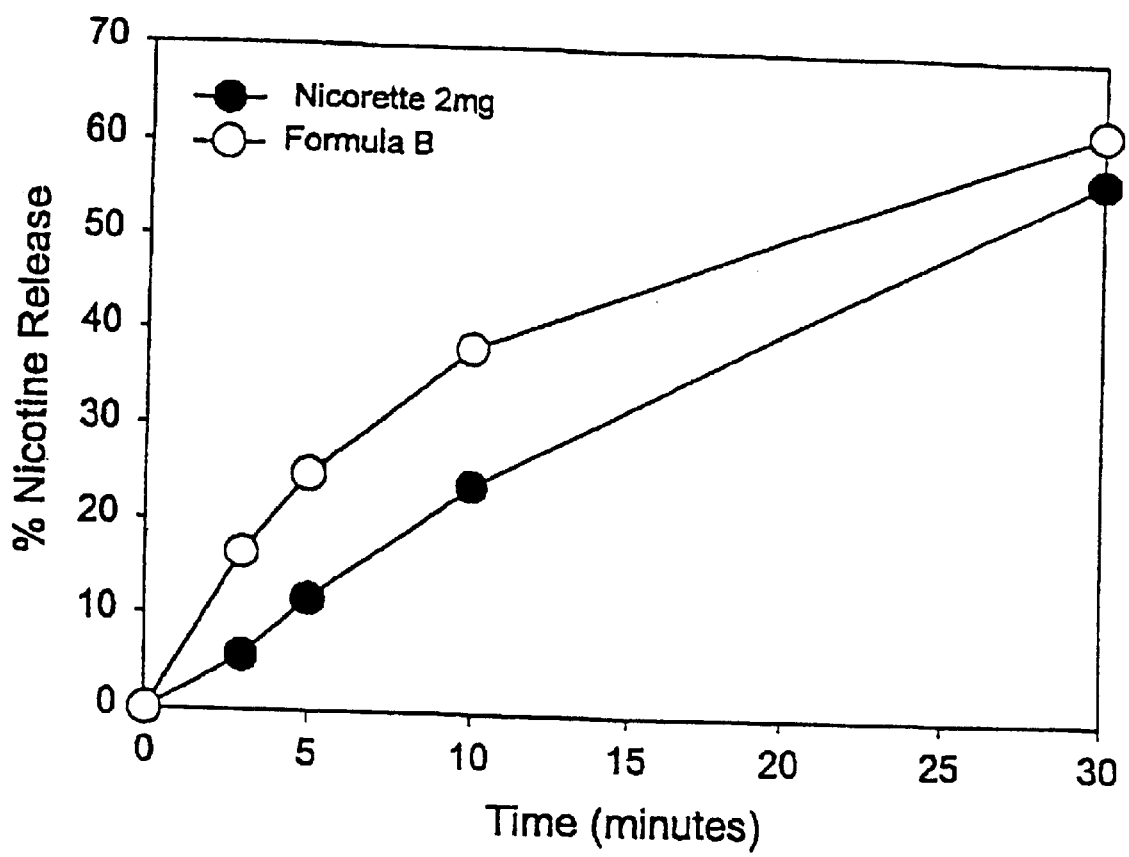

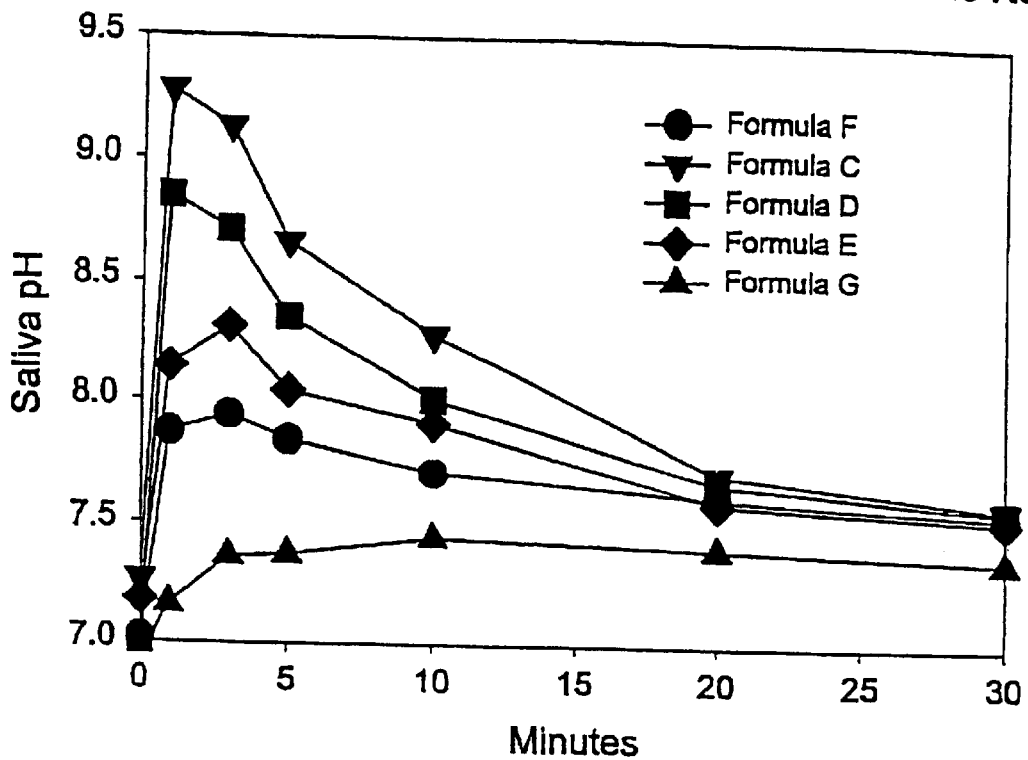
Figure 3: Effect of Buffer Content on pH and Nicotine Release

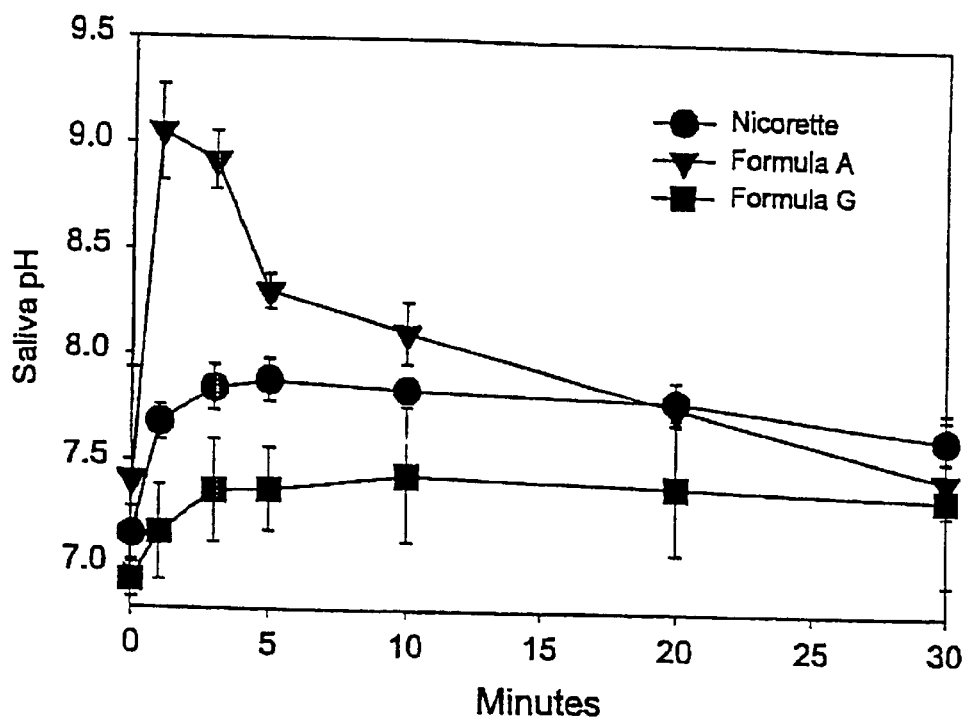
Figure 4: pH profiles for Formula A, Formula G, and Nicorette 2mg

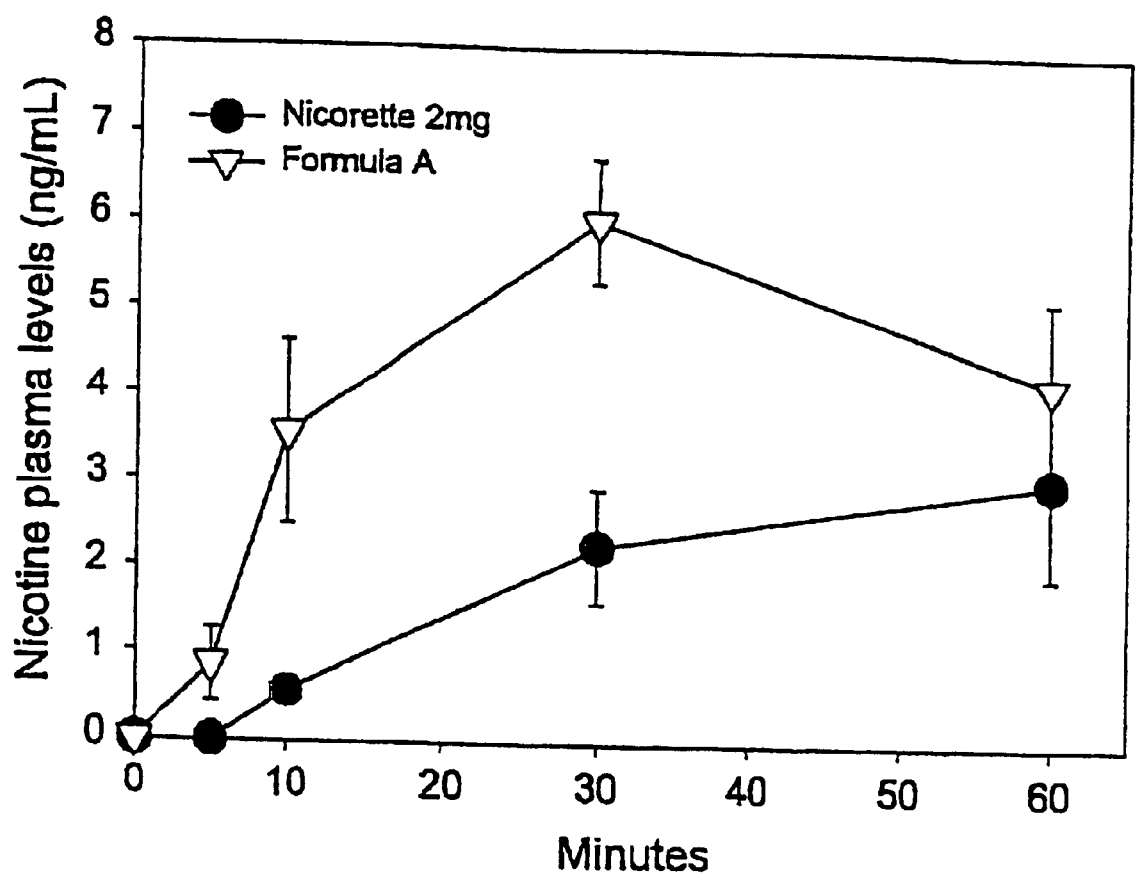

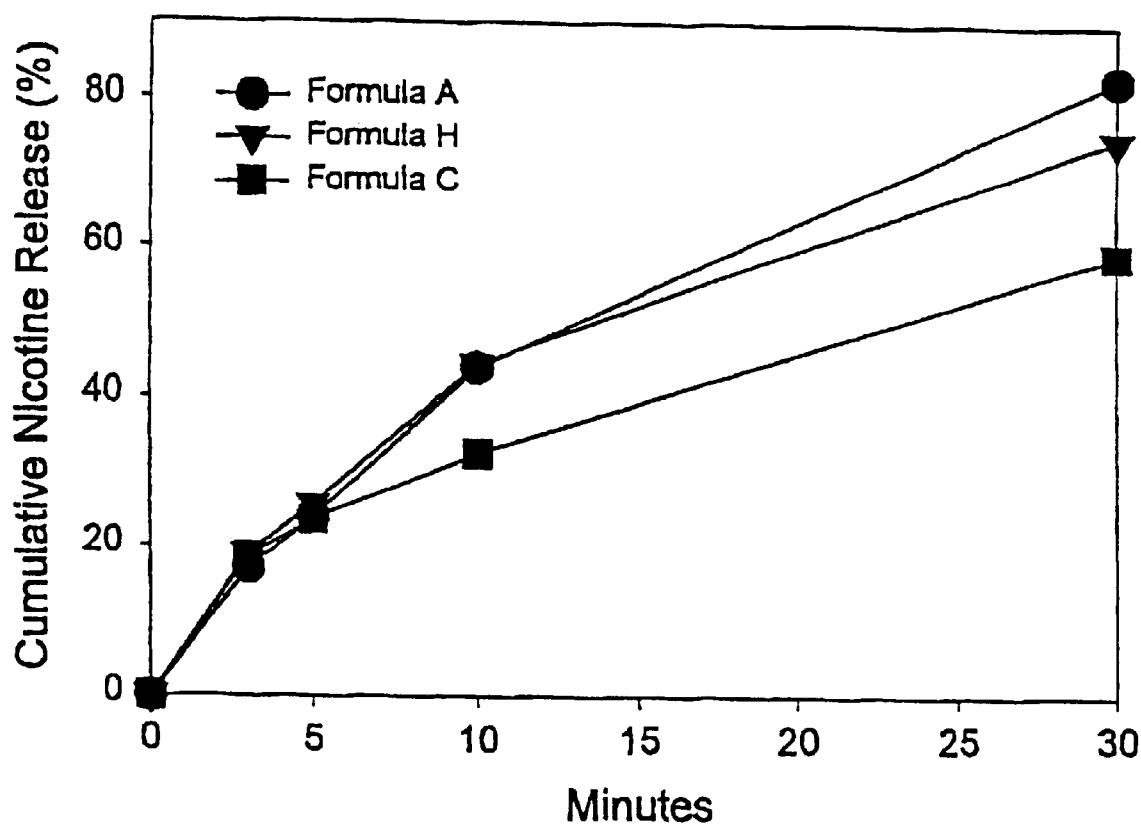

% NICOTINE RELEASE

MEDICATED CHEWING GUM DELIVERY SYSTEM FOR NICOTINE

This application is a continuation-in-part of U.S. Ser. No. 09/146,696, filed Sep. 3, 1998.

FIELD OF THE INVENTION

The present invention relates to medication delivery systems, and more specifically to nicotine delivery systems, and particularly to a nicotine chewing gum delivery system that provides for an improved nicotine release profile over existing systems.

BACKGROUND OF THE INVENTION

Delivery systems containing actives for oral administration now include various chewing gum formulations. Chewing gums permit release of the active over time as the gum product is masticated, or chewed. The action of saliva on the gum further facilitates release of the active, as well as its subsequent absorption by the mucous membranes lining the mouth, throat, larynx and esophagus.

A problem with many chewing gum formulations is that they fail to deliver an adequate dosage of medicament or active in the appropriate manner over the entire dosing interval. This results in insufficient active being absorbed into the bloodstream for effective therapeutic or pharmacological actions. There are many reasons for inadequate dosing. Many chewing gum formulations release active medication slowly over time in a more or less continuous fashion. These formulations may also retain a significant portion of the active during the prescribed dosing period, resulting in inadequate dosing of the patient. Further, the particular gum base material chosen to contain and subsequently release the active material may not perform optimally. The gum base may be difficult to chew or unusually hard, thereby damaging the teeth and gums. The art has not suggested the appropriate gum base formulation, as well as other non-actives, which can be most successfully utilized in combination with a particular type of active. It has therefore proven quite elusive to find the right qualitative and quantitative parameters for both actives and non-actives in the delivery system which will ensure a reliable release rate for the active substance.

Another reason that certain chewing gum formulations have not proven efficacious is because they are not properly pH regulated. We have found it necessary to generate a particular pH, and specifically a relatively alkaline pH in the mouth, to allow for the proper release and absorption of many types of actives, i.e., drugs containing a basic nitrogen moiety in their chemical structure. Formulating the appropriate chemistry that will not only generate the proper pH, but do so over the entire release period, and do so without overwhelming the consumer has proven to be quite difficult.

As a result of the foregoing problems, many delivery systems for active substances provide relatively ineffective release profiles. This is unfortunate since many actives would be quite amenable to a delivery system such as chewing gum, especially those that enter the body through the mucous membranes lining the oral cavity, thereby avoiding first-pass metabolism that occurs with many oral formulations. Nicotine is one such example.

Nicotine is a highly addictive chemical stimulant present in cigarettes. Most smokers find achieving and maintaining abstinence to be difficult, and attempts to quit often fail. The emergence of craving for nicotine and of nicotine withdrawal symptoms makes sustained cessation difficult. Providing nicotine by medication is a proven method of smoking cessation, but one with limited success. Nicotine replacement is considered to work by relieving craving and symptoms of withdrawal. Nicotine medications can affect craving in two ways:

1. By providing a relatively steady level of nicotine in the bloodstream, such medications can prevent or blunt craving throughout the day. For this purpose, a medication that provides steady sustained release and that maintains blood levels is most desirable.
2. Smokers are also subject to episodic peaks or surges of craving, typically evoked by internal or external stimuli. Research has shown that these episodes often lead to relapse. Rapid relief of craving in such episodes is expected to help prevent relapse. Acute delivery of nicotine via the oral mucosa may help relieve cravings, with the speed of relief being a function of the speed of delivery of nicotine into the blood stream.

To help these future ex-smokers, various nicotine replacement formulations have been devised. These are designed to sate an individual's physiological cravings for nicotine with a measured dosage of the drug. For example, U.S. Pat. No. 5,824,334 is directed to a tobacco substitute in which the user places a nicotine dosing unit in and out of the mouth to simulate actual smoking. Certain commercial regimens allow for successively reduced levels of nicotine over a period of time which permit a person to quit smoking gradually without going "cold turkey". In this way, the smoker's cravings for nicotine are dissipated slowly over several days or weeks.

Some nicotine dosing compositions have been formulated into a confectionery type of composition. Of these, chewing gums are often particularly preferred. The physical action of chewing allows an individual to simulate the oral response associated with the smoking habit, while the biting and grinding action results in release of nicotine over time. Examples of confectionery preparations containing nicotine are found in the disclosures of U.S. Pat. Nos. 3,877,468, 3,901,248, 5,488,962, as well as in WO 97/33581.

U.S. Pat. No. 3,877,468 is directed to a smoking substitute/chewing gum composition which is acidified by directly incorporating a pharmacologically acceptable organic or inorganic acid into the formulation. U.S. Pat. No. 3,901,248 seeks to provide a nicotine release rate that is substantially uniform over time. The patent's objective appears to be the avoidance of a nicotine release and absorption rate that may be too fast.

If a particular gum fails to provide a desired level of craving relief, attempts to obtain additional nicotine from the gum may cause increased feelings of nausea. This may occur because of the frequent failure of gum formulations to allow effective absorption of the nicotine in the mouth. Instead, a significant portion of the nicotine released may be swallowed, thereby causing stomach upset and nausea. Thus, it may be difficult to self-adjust the modest effectiveness of conventional nicotine delivery gums without increasingly experiencing nausea.

Despite the disadvantages associated with conventional nicotine delivering gum, there are commercially available versions of nicotine gum, one of which is marketed using the trademark NICORETTE®. This commercially available gum utilizes the "park and chew" method to provide nicotine release. The consumer bites down on a piece of gum, then parks the gum inside the mouth for a period, and then repeats this regimen to obtain further release of nicotine. Nicotine is released in a steady, slow manner, and thus is highly dependent on conscious chewing actions by the user.

Although the sensory effects of Nicorette provide an initial level of craving relief which is comparable to that which is produced by confectionery chewing gum, it is the delivery of nicotine to the bloodstream which produces objectively documented effects of craving relief. The delivery of nicotine to the bloodstream generally provides discriminable effects to the user (e.g., "feel the drug"), reduced desire for smoking, restoration of cognitive performance, and reversal of withdrawal-associated EEG disruption.

Studies on the effects of Nicorette provide a basis for determining the doses at which various effects occur. For example, the approximately one milligram of nicotine delivered over 15–30 minutes by the 2 milligram version of Nicorette provides detectable effects, with minimal risk of nausea and undesirable pharmacological consequences for most users. When the dose is increased, for example by using the 4 milligram version of Nicorette (which delivers about 2 milligrams of nicotine) or by administering multiple units of Nicorette (up to 4 units of the 4 milligram version of Nicorette), the likelihood of the craving reduction increases, but the probability of undesirable consequences, such as dizziness and nausea, also increases.

Besides experiencing some chronic level of craving, research has indicated that smokers also experience periodic and episodic peaks or surges of craving. Unless treated, these episodes, often provoked by situational or internal stimuli, may lead to relapse. Some acute treatments for craving are behavioral; for example, it is often recommended that smokers eat or chew something, perhaps to distract their attention. It has also been proposed that acute doses of nicotine could treat or satisfy craving, much as smoking a cigarette can. The efficacy of orally-administered nicotine (via Nicorette chewing gum) for relief of such craving has been confirmed by at least one recent study. After craving had been provoked through a laboratory procedure, smokers who chewed nicotine-containing gum experienced more and faster craving relief than smokers who chewed a confectionery gum. Chewing a gum, whether containing nicotine or not, had an initial effect on craving. The incremental effect of chewing an active nicotine-containing gum becomes evident only after 15–20 minutes, when that gum formulation begins delivering substantial nicotine to the bloodstream. Acute administration of nicotine can provide acute relief of craving, because the speed and effectiveness of relief is a function of how quickly nicotine is delivered to the bloodstream. Rapid relief of craving is vitally important to clinical outcome for two reasons:

1. By providing rapid positive feedback, it reinforces use of the medication.
2. If craving relief is not provided quickly, these episodes can quickly lead to relapse. The average episode of temptation may last only about 15 minutes.

It appears that the craving-reducing effects of nicotine on the body are almost exclusively due to the nicotine which is absorbed into the bloodstream. Nicotine which remains in the saliva and/or is swallowed has very little effect beyond its flavor-induced sensory effects and stomach upset produced by excessive amounts of swallowed nicotine.

Nicotine from NICORETTE reaches the bloodstream in several different ways. About 50% of the nicotine from the 2 and 4 milligram versions of the Nicorette is released from the gum during chewing. The rest of the nicotine typically remains in the gum and is discarded by the user.

Of the nicotine delivered by the 2 milligram version of the Nicorette gum to the saliva, about 0.8 milligram may be absorbed through the membranes of the mouth (the buccal mucosa) and appear in the bloodstream. The remaining approximately 0.2 milligram is swallowed, of which 0.06 milligram survives the first pass effects of hepatic metabolism and appears in the bloodstream. The 4 milligram version of Nicorette gum achieves nicotine absorption values which are approximately twice those of the 2 milligram version.

Although the amount of nicotine absorption from NICORETTE is related to the chewing rate and the time the saliva is held in the mouth, these variables are significant only at the extremes of rapid versus slow chewing action, and frequent versus infrequent swallowing. Outside of such extremes, these variables have very little impact on nicotine absorption. Thus, it takes approximately 10 to 30 minutes to achieve adequate blood levels of nicotine from Nicorette, regardless of whether the "park and chew" (or "chew and park") method is used or chewing at regular intervals e.g., one chew per 4 seconds).

A delay of 10 minutes or more in the release and absorption of nicotine, however, may be excessively long for someone who is trying to quit smoking. This critical time period is the time during which the smoker would normally be receiving nicotine if the smoker began smoking a cigarette. Thus, it is desirable for nicotine replacement therapies such as nicotine gum to provide adequate nicotine dosing within 10 minutes of the onset of craving. A product that delivers nicotine too slowly will be ineffective for relapse prevention. In practice, most commercial products simply fail to deliver an adequate dosing of the medication, especially early in the administration process, i.e. within a few minutes of administration. Because nicotine is potentially toxic and addictive, many makers of nicotine chewing gums choose a nicotine release rate which, in its commercial embodiment, is simply too slow to be effective. The result many times is a product that the smoking customer finds highly ineffective in reducing his or her cravings.

There is consequently a need in the art for an improved delivery system for actives such as nicotine. More specifically, there is a need for an improved chewing gum delivery system that provides a rapid release rate for nicotine, early in the chewing process. A nicotine delivery product is needed which, in its physical embodiment, is highly efficacious in releasing a specified, effective quantity of the stimulant shortly after administration, followed by slower sustained release over an extended period thereafter. Also needed is a formulation that is not as chewing dependent as certain commercial compositions. At the same time, the gum should be chewer-responsive, i.e. capable of being manipulated to release nicotine at a faster rate with faster chewing and less nicotine with slower chewing. Further desirable is a formulation that will provide the user with adequate blood levels of nicotine soon after onset of chewing for suppression of cravings and withdrawal symptoms. A rapid achievement of adequate blood levels of nicotine over the first ten minutes of chewing would move the product toward a closer approximation of the nicotine blood levels delivered by smoking a cigarette. At the same time, a release profile similar to that delivered by smoking a cigarette is not desirable because of the risk of producing a product that could readily be abused. With a formulation that rapidly releases limited amounts of nicotine over the first 10 minutes of chewing in a form that is readily absorbed into the bloodstream, the smoker can obtain relief of cravings quickly, before relapse occurs. The final formulation also should be easy to administer and have highly suitable organoleptic properties that would enhance its use. The product also should contain a demonstrably reliable buffer system which will help to maintain a proper pH inside the oral cavity to permit absorption of the active nicotine compound.

SUMMARY OF THE INVENTION

The present invention can be configured to provide an initial rapid release of medicine over the first few minutes of chewing followed by slower release over a period of 30 minutes or more. The improved rapid release of medication preferably is accompanied by release of buffer that allows for rapid absorption of active from the mouth into the bloodstream, resulting in initial higher blood levels of medication and corresponding faster relief of symptoms, such as cravings and withdrawal symptoms.

The objects of the invention can be provided in the form of a nicotine delivery system that preferably comprises a chewing gum. The chewing gum composition of the invention contains a gum base matrix and preferably a tobacco alkaloid such as nicotine as the active. The formulation hereinafter described desirably releases at least about 15%, more desirably at least about 20%, and preferably at least about 25% or even more of its nicotine content within about 3–5 minutes of mastication or preferably even less time (as those terms are used herein, "chewing" and "mastication" refers to continuous chewing, grinding or gnashing action, as well as to a regimen of chewing followed by a period of inactivity, which is followed by chewing again, and the like).

In some embodiments hereinafter described, a composition according to the present invention can deliver at least about 40–50% of its nicotine content within about 3–5 minutes, or even less time, as for example about 1–2 minutes. As a result, a loaded nicotine concentration in the bloodstream of about 2 to 5 nanograms of nicotine per milliliter of blood can be achieved within about 10 minutes. The delivery system also can provide continued release of nicotine over the next 20 minutes or so of chewing. The overall release pattern provided by this formulation is considered a form of sustained release delivery system.

The present invention therefore can be configured to provide a sustained release formulation that initially releases an active upon initial chewing over a period of 1–10 minutes, and that follows the initial release with a continued release of active that occurs with further chewing over 20 minutes or so. Although a majority of active is released by the physical act of biting the gum together with the leaching action of saliva, there is some release of active that occurs when the gum formulation is not chewed, but the leaching action of saliva continues. This pulsatile pattern of release of active that occurs as the gum is chewed followed by a pause and subsequent slower release of active is somewhat different from the more conventional pattern of sustained release obtained with other commercial formulations, e.g., controlled release capsules, in which release of active occurs in a more continuous manner.

In another preferred embodiment of the invention, the nicotine delivery chewing gum composition desirably delivers about 60% of its nicotine content within 10 minutes of mastication. It is further contemplated that the chewing gum release up to about 90%, and more preferably about 100% of its nicotine content within about 50 minutes, more desirably within about 30 minutes. In this way, a prolonged loaded concentration of nicotine of at least about 3 nanograms per milliliter of blood is maintained for at least about 20 minutes, more preferably about 30 minutes, and even more desirably about 60 minutes after use begins.

By thereby providing an initial significant burst of nicotine, the formulation more closely approximates the smoking experience and sensation smokers feel after first lighting up and then dragging on a cigarette, cigar, pipe or other tobacco product for about 3–5 minutes or so. Importantly, the composition herein described provides further sustained release of the drug throughout the course of chewing for up to about 30 minutes or even longer.

In another embodiment of the invention, a nicotine chewing gum delivery system provides an optimal combination of nicotine together with a buffer system. The buffer system raises pH levels in the mouth to as much as about 9.0 within the first few minutes of chewing. This results in a greater conversion of nicotine to its free base form, which in turn facilitates nicotine absorption in the buccal cavity. The rapid early release of nicotine as described above, together with release of buffer in the oral cavity, allows attainment of nicotine blood levels sufficient to provide the chewer with early craving relief in a superior manner to existing nicotine gum formulations. At the same time, continued release of nicotine over the course of about 30 minutes keeps the nicotine concentration in the bloodstream at or near a pharmacologically effective concentration.

The composition in all its embodiments can be soft and pliable inside the mouth, both upon initial chew and after prolonged mastication. It is highly preferable that the formulation be substantially non-liquid as well.

Still another aspect of the invention is a method of smoking cessation or of reducing cigarette smoking which comprises the administration of the nicotine delivery system herein set forth. A method of nicotine administration involves the mastication of the composition herein described.

BRIEF DESCRIPTION OF THE DRAWINGS

FIG. 1A is a graph comparing a cumulative nicotine release profile of a first exemplary embodiment of the present invention to that of a commercially available nicotine gum.

FIG. 1B is a graph comparing a nicotine release rate of the first exemplary embodiment of the present invention to that of a commercially available nicotine gum.

FIG. 2 is a graph comparing a cumulative nicotine release profile of a second exemplary embodiment of the present invention to that of a commercially available nicotine gum.

FIG. 3 is a graph of salivary pH achieved over time in response to separate chewing of exemplary embodiments of the present invention.

FIG. 4 is a graph of salivary pH achieved over time in response to separate chewing of the first exemplary embodiment, one of the exemplary embodiments associated with FIG. 3, and a commercially available nicotine gum.

FIG. 5 is a graph of nicotine plasma levels achieved over time in response to separate chewing of the first exemplary embodiment and the commercially available nicotine gum.

FIG. 6 is a graph comparing cumulative nicotine release profiles of a the first exemplary embodiment of the present invention to that of other exemplary embodiments.

DETAILED DESCRIPTION OF THE PREFERRED EMBODIMENTS

Figure 7:
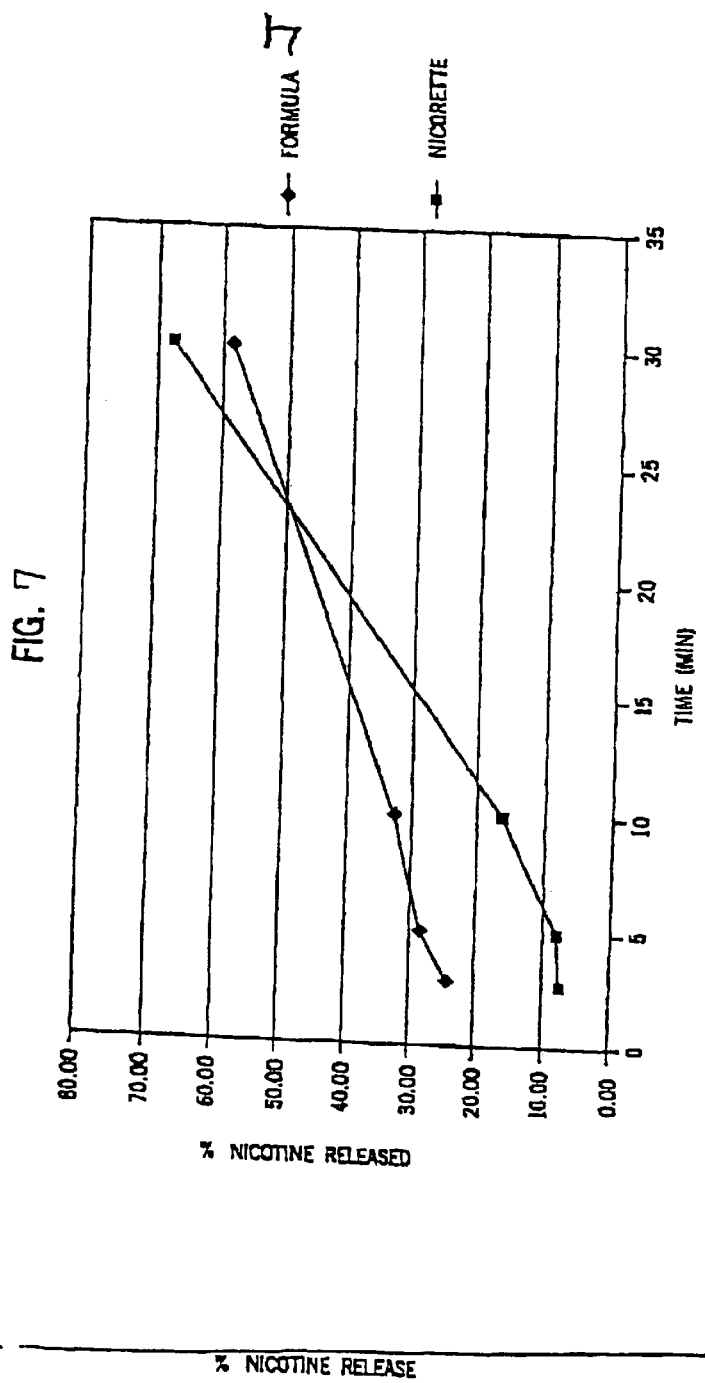
FIG. 7 is a graph comparing cumulative nicotine release profiles of a first exemplary non-butyl rubber-based embodiment of the present invention to a commercially available nicotine gum.

An exemplary implementation of the present invention as a nicotine delivery system is designed to permit a systemic and highly reliable release of active nicotine compound inside the body and especially the mouth and buccal cavity. While other forms may be contemplated by those skilled in the art and are within the scope set forth herein, the nicotine delivery system is preferably in the form of a chewing gum.

The chewing gum comprises a gum base matrix as a major component. The gum base matrix will include at least one gum base material which may be selected from the many water- and saliva-insoluble gum base materials known in the art. Illustrative examples of suitable polymers for gum bases include both natural and synthetic elastomers and rubbers, as well as mixtures thereof. Naturally-derived polymers include, for example, substances of plant origin like chicle, jelutong, gutta percha and crown gum. Synthetic elastomers such as butadiene-styrene copolymers, isobutylene and isoprene copolymers (e.g., "butyl rubber" in the art), polyethylene, polyisobutylene, polyvinylesters such as polyvinylacetate, and mixtures of any of the foregoing may be particularly useful.

In one embodiment, it is highly preferable that the gum base be selected so as to provide a final chewing gum composition which has a relatively "soft" chew both at the onset of mastication, as well as towards the end of the chewing process (about 20 to 30 minutes or so). Another desirable characteristic of the gum base should be its ability to facilitate the early release over the first 10 minutes of up to 60% of the active nicotine ingredient(s), hereinafter described, as well as early release of sufficient buffer to raise the pH of mouth saliva to the range of pH 8–9. Release of nicotine and buffer should continue at a slower rate over the next 20 minutes or longer of chewing. Thus, one or more gum base materials that are at least partially hydrophilic in nature are especially desirable. It is even more preferred that the material have significant hydrophilic characteristics. Of these types of material, polyvinylacetate is particularly preferred. Especially preferred is low to medium weight polyvinylacetate. Polyvinylacetate having a molecular weight (MW) of about 12,000 to 45,000 is even more desirable. In an especially desirable embodiment of the invention, the amount of polyvinylacetate (PVA) in the gum base is maximized with no butyl rubber present, and the quantity of non-PVA polymers such as butadiene-styrene, butylene-based polymers and copolymers is preferably minimized. It has now been discovered that inclusion of polyvinylacetate provides a gum base which yields a softer, less brittle and less sticky nicotine-chewing gum composition, thereby contributing to a more organoleptically pleasing chewing sensation. Polyvinylacetate also tends to be more hydrophilic in nature, and may allow for better release of the saliva-soluble ingredients from the gum composition, referred to in more detail below.

In another preferred embodiment of the invention, the type of gum base utilized includes at least some butyl rubber (copolymer of isoprene and isobutylene), with additional amounts of polyisobutylene, and with polyvinylacetate (preferably PVA having a MW of approximately 12,000) also being present. This butyl-rubber based material appears to have certain advantages when used together with nicotine in the form of a salt, as hereinafter described.

The gum base matrix (in whatever embodiment) will typically comprise from about 40 to 90% of the total chewing gum composition of the invention (unless otherwise stated, all percentages provided herein are weight percentages, based on either the total weight of the gum base matrix or of the final chewing gum composition, where noted). It is more preferred to utilize less than about 70% by weight of chewing gum base matrix material. In certain embodiments too much gum base may interfere with the release of the active tobacco alkaloid material, and additionally, may contribute to tackiness and poor mouth-feel of the final product. In an especially preferred embodiment of the invention, the chewing gum composition will contain about 50 to 60% of gum base matrix, and desirably about 55%. Of the foregoing amounts, about 25–75% thereof, more preferably about 30–60% thereof, will be the gum base polymer material(s) heretofore described.

An especially preferred gum base matrix formulation will therefore include polyvinylacetate having a molecular weight of about 12,000 (about 14% of the total chewing gum composition), polyisobutylene (about 5% of total), and butyl rubber (about 4% of total). Together these polymers will comprise about 35–45% by weight of the gum base matrix, most preferably about 40%.

The gum base matrix may additionally contain other ingredients well known in the art and selected from the group consisting of plasticizers and softeners to help reduce the viscosity of the gum base to a desirable consistency and to improve the overall texture and bite. These compounds are also noted for their emulsifying properties. As non-limiting examples, compounds such as lecithin, mono- and diglycerides, lanolin, stearic acid, sodium stearate, potassium stearate, glycerol triacetate, glycerol monostearate and glycerin are provided. Stearic acid, lecithin and mono- and diglycerides are particularly preferred. Plasticizers and softeners are desirable as part of the formulation because in addition to softening the primary gum base polymeric compound, they also seem to facilitate release of the active upon mastication. When added, the plasticizers and softeners will comprise from about 0.1 to 20% of the gum base matrix formulation, and more desirably will be within the range of about 5–15% thereof.

Waxes such as beeswax and microcrystalline wax, and fats/oils such as soybean and cottonseed oils are also contemplated as part of the gum base formulation. These compounds also function as softening agents. Typically, these compounds (either alone or in combination) will comprise from zero up to about 25% of the gum base matrix, and even more desirably will constitute less than about 20% of the gum base matrix, and more preferably will make up about 15–20% by weight of the gum base matrix. An especially desirable formulation will include a combination of microcrystalline wax and partially hydrogenated soybean oil in an approximate 1:2 weight ratio. A more exhaustive listing of these compounds, along with recommended weight percentages, may be found in any available industry reference.

Other materials which may be included as part of the gum base matrix include elastomer solvents. These are typically selected from the group consisting of rosin and resin material typically utilized in the confectionery chewing gum industry. Examples include methyl, glycerol, and pentaerythritol esters of rosins or modified rosins, such as hydrogenated, dimerized or polymerized rosins or mixtures thereof. More specific examples include pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene, and terpene resins including polyterpene and mixtures thereof. Elastomer solvents can comprise from about zero to 75% of the gum base. It is preferable, however, to minimize or even eliminate the quantity of rosin/resin in the gum base. It is especially desirable not to exceed about 10% by weight of the gum base matrix with rosin/resin compound(s).

Filler material may also be present in the gum base matrix as part of the composition of the invention. This material is further selected to enhance the chewability of the final chewing gum composition. In at least some embodiments, certain filler material may also enhance the release and absorption of nicotine and other tobacco alkaloids. Those fillers which are substantially non-reactive with other components of the final formulation are also preferred. Desirable filler materials will therefore include calcium carbonate, magnesium silicate (talc), as well as dicalcium phosphate, and any mixtures thereof. Particularly preferred may be dicalcium phosphate. Other metallic mineral salts may also be utilized as filler material, as for example alumina, aluminum hydroxide, and aluminum silicates, provided they possess the characteristics heretofore set forth. Filler material will typically comprise about 0.1 to 30% of the gum base matrix, and more preferably will be within the range of about 10 to 20% thereof.

Trace amounts of standard industry preservatives such as butylated hydroxy toluene (BHT) may also be present in amounts less than about 0.1% or so of the gum base.

Further provided as part of the nicotine delivery system, chewing gum formulation of the invention is at least one bulk sweetener. This material is added to the composition to impart improved palatability to the chewing gum composition, and thereby provide a pleasant chewing experience to help in masking the bitter, acrid taste of nicotine. The "sweetener" may or may not be perceptibly sweet. Examples of sweeteners include those compounds selected from the group consisting of saccharide material such as the mono-, di-, tri- and polysaccharide materials available in the industry, including oligomers, and oligosaccharides. As non-limiting examples, sugars such as sucrose, glucose (corn syrup), dextrose, invert sugar, fructose, and mixtures thereof may be useful. Less or non-sweet sugars and polysaccharide material such as maltodextrin and polydextrose may also be utilized. In certain embodiments of the invention, however, "sugar-free" or "non-sucrose" formulations may be especially desirable. Thus, natural and synthetic non-saccharide-based sweetners may be selected from the group consisting of saccharin and its various salts such as the sodium and calcium salts, cyclamic acid and its various salts, dipeptide sweeteners, chlorinated sugar derivatives such as sucralose, dihydrochalcone, glycyrrhin, Stevia rebaudiana (Stevioside), and sugar alcohols such as sorbitol, sorbitol syrup, mannitol, xylitol, hexa-resorcinol and the like, including mixtures of any of the foregoing, are contemplated for use herein. Hydrogenated starch hydrolysate, (lycasin), and the potassium, calcium and sodium salts of 3,6-dihydro-6-methyl-1-1,2,3-oxathiazin-4-on3-2,2-dioxide are also within the scope of the invention as sweetener material. Of the foregoing, sorbitol and xylitol are particularly preferred, either alone or more desirably in combination. Xylitol may be desirable because of its non-cariogenic or anti-cariogenic properties.

The bulk sweetener(s) will make up about 20 to 75% of the chewing gum composition of the invention. It is more preferable to include one or more sweeteners within the range of about 25 to 40% of the final formulation, even more desirably about 30 to 35% of the gum composition. Also preferred is to utilize a combination of at least two sweeteners in an approximate 1:1 weight ratio.

In addition to the bulk sweetening material, the composition of the invention also comprises one or more flavoring agents. These may be selected from any of the industry-available natural and synthetically-derived food and pharmaceutical flavors in whatever form. Especially preferred are those materials which impart a cooling and/or vaporizing sensation to the consumer upon mastication of the gum. As non-limiting examples, peppermint, spearmint, wintergreen, cinnamon, menthol and menthone flavors, oils and derivatives are desirable. Other compounds are contemplated as well which may impart a physiological or psychological calming or cooling sensation to the user who is trying to quit smoking. For example, those flavors which mimic the taste of tobacco are also within the scope of the invention. Food and pharmaceutical grade coloring agents available throughout the industry may also be utilized. Any of the foregoing flavor and coloring agents, either alone or in combination will typically comprise from about 0 to 10% of the chewing gum composition, more preferably from about 0.1 to 5%, and even more desirably about 2 to 3% thereof. It is also within the scope of the invention that the formulation specifically not contain any adjunct flavors or colors. These embodiments may be preferred to avoid making the final product in any way attractive or enticing to non-smokers, e.g. children.

The nicotine delivery system of the invention also comprises one or more active ingredients. At least one active ingredient is selected from the group consisting of tobacco alkaloids. Tobacco alkaloids include nicotine and nicotine-like or related pharmacologically active compounds such as nor-nicotine, lobeline and the like, as well as the free base substance nicotine and all pharmacologically acceptable salts of nicotine, including acid addition salts. "Nicotine" as that term is used herein therefore includes all the foregoing tobacco alkaloids. Of these, the nicotine salts are useful and can include, for example, nicotine hydrogen tartrate and nicotine bitartrate, as well as nicotine hydrochloride, nicotine dihydrochloride, nicotine sulfate, nicotine citrate, nicotine zinc chloride monohydrate and nicotine salicylate, either alone or in combination. Of the foregoing, nicotine hydrogen tartrate and nicotine bitartrate may be especially suitable. In addition, "nicotine" also includes the solid complex of one or more tobacco alkaloid compounds bound to an ion exchange resin or other polymer release system, particularly a cation exchanger. An exhaustive listing of nicotine ion exchange resins and their chemistry is readily available from various sources in the industry, and the skilled artisan may consult Lichtneckert et al., U.S. Pat. No. 3,901,248, for a further discussion and listing thereof. Nicotine polacrilex as a nicotine ion exchange resin may be especially desirable for use with the chewing gum composition of the invention, according to one embodiment hereof. It has been conventional thinking in the industry to utilize ion exchange nicotine resins for a slower release of nicotine, while nicotine salts have been favored for faster dissolution and release of the compound. The inventors herein have discovered just the opposite effect, however, in their non-butyl rubber, polyvinylacetate gum base formulation. The use of an ion exchange resin, e.g. nicotine polacrilex, in the non-butyl rubber, polyvinylacetate gum base formulation results in a faster initial nicotine release profile than commonly produced by commercial formulations, e.g. Nicorette.

The hydrophilicity of the PVA in combination with a suitable buffer system may contribute to the release of nicotine from its polacrilex substrate. This finding, while unconventional in the art, is consistent with the inventors' attempts to formulate a nicotine chewing gum that provides a rapid release of the compound within the first few minutes after mastication. This, in turn, more closely approximates the smoking experience.

In still another embodiment of the invention, an efficacious release of nicotine is obtained if a salt thereof is utilized in conjunction with a butyl rubber-based gum base matrix (together with PVA), as heretofore described. Thus, nicotine hydrogen tartrate or bitartrate, either alone or in combination with nicotine polacrilex, may be particularly preferred in conjunction with this butyl rubber-based gum material. The inclusion of some PVA in the butyl rubber-based formulation may further act synergistically on the nicotine release rate for the nicotine salts.

A serving, hereinafter described, of the nicotine chewing gum composition of the invention will preferably contain about 0.1 to 10 milligrams of nicotine (as measured in its free base form). More desirably, the amount of nicotine will be within the range of about 1 to 10 milligrams, and even more preferably, be within the range of about 1 to 5 milligrams. In some embodiments, it may be particularly preferred to include about 1–4 milligrams of nicotine in a serving, with perhaps 2 milligrams being especially desirable. Of the foregoing amounts, the skilled artisan may choose to add extra nicotine, preferably up to about 10–25% or so by weight. This extra amount may be regarded as overage, that is, the amount which may be expected to be "washed away" or otherwise not released or absorbed during mastication. As a weight percentage, the total amount of nicotine (in whatever chosen form, measured as per its free base form) will typically comprise about 0.01 to 10%, and more preferably be within the range of about 0.1 to 1% of the chewing gum composition. It may be especially desirable to utilize about 0.25 to 0.8% of nicotine by weight, with about 0.35% being especially preferred. The foregoing percentages will vary depending upon the particular source of nicotine utilized, the amount of nicotine the skilled artisan desires to include in the final formulation, as well as on the particular release rate of the nicotine or nicotine resin complex desired.

Nicotine as an active ingredient may also be provided in the form of an encapsulation. An encapsulated nicotine matrix may provide for more content uniformity in the final formulation. Encapsulation may also impart a greater degree of stability to the active during relatively prolonged periods of commercial storage. Encapsulating nicotine can further enhance the hydrophilicity of the less water-soluble versions of the compound, and can also act to regulate the dissolution of the more highly soluble forms of the drug. Encapsulation may be accomplished by methods known in the art. In order to effectively encapsulate the active nicotine drug, one or more food-grade materials are employed as processing aids. These edible materials can include oleaginous substances (fats and oils), as well as saccharides, proteins and other non-toxic polymeric material, especially those with emulsifying properties. Highly suitable encapsulation processing aids are preferably oleaginous material and any one or more oleaginous food and pharmaceutical grade materials may be utilized for this purpose. It is believed that the oleaginous and other encapsulating material surrounds and enrobes individual particles of the active substance, thereby creating a matrix of several thousand or more individually enrobed particles once combined into the final chewing gum composition.

Especially suitable oleaginous encapsulating material includes various food-grade oils and fats available in the industry. Of these, those with emulsifying properties are particularly preferred. Vegetable and animal oils and fats may be utilized for this purpose. Stearine, for example, may be utilized as an encapsulating agent, while certain mono- and diglyceride-based fat products are also efficacious. Canola, cottonseed and soybean oils may be preferred as well in certain embodiments. Also useful is one or more medium chain triglyceride (MCT) oils, as well as other mono-, di- and triglyceride-based fatty acid oils. When utilized, the encapsulating material will typically comprise about 0.1 to 40% of the nicotine chewing gum delivery system, and more desirably, will be within the range of from about 0.1 to 15% thereof. In addition to the active nicotine substance, it is also within the scope of the invention that any of the other ingredients constituting the final formulation, including any flavorants or even buffer material, hereinafter described, be encapsulated as well.

Low and high shear mixing apparatus are especially useful for preparing nicotine encapsulations. Spray-drying and extrusion methods are also available. Other highly suitable methods include flash-flow processing as described in U.S. Pat. Nos. 5,236,734, 5,238,696, 5,518,730, 5,387,431, 5,429,836, 5,549,917, 5,556,652, 5,582,855 and most recently, U.S. Pat. No. 5,834,033. In particular, U.S. Pat. No. 5,380,473, sets forth a process in which the temperature of a nonsolubilized feedstock carrier is increased to a point where it will undergo internal flow, followed by ejecting a stream of the feedstock and then subjecting it to disruptive fluid shear force which separates it into separate parts or masses which have a transformed morphology. Also disclosed in U.S. Pat. No. 5,380,473 is an apparatus with a high pressure nozzle for changing the morphology of the feedstock.

Another ingredient included as part of the nicotine chewing gum delivery system of the invention is a buffer material or system. Buffering agents are those compounds that assist in release and conversion of the nicotine salts (ionized nicotine) to nicotine free base (unionized nicotine). Passage of actives across the mucous membranes inside the mouth to the bloodstream and to target tissues is due primarily to passive diffusion of the unionized form of the active. To be effective the buffer material should be released in sufficient amounts with the release of the active to create a basic or alkaline pH environment inside the mouth, thereby facilitating effective delivery to target organs. Consequently, conversion of nicotine in the chewing gum into freebase nicotine in mouth saliva is an important step in providing smokers with adequate blood levels of nicotine to reduce craving. Buffer compounds assist with this conversion by raising the pH and thereby facilitating nicotine absorption.

Of these buffers, certain salts, for example, sodium carbonate, sodium bicarbonate, potassium carbonate, potassium bicarbonate, potassium citrate and dipotassium phosphate, or mixtures thereof, are particularly preferred. In certain embodiments, especially with butyl rubber-based gum base formulations, potassium carbonate alone may be especially desirable as a pH buffering agent. The buffering agent will comprise about 0.1 to 10% of the nicotine delivery system chewing gum formulation, and desirably will be within the range of about 0.5 to 5% thereof. In particular, about 2 to 5% quantity of buffer may be especially desirable in the final formulation. On a weight basis, the buffer will usually comprise about 10–60 mg. in a 1 gram serving of final product. More preferably, there will be about 25–60 mg., and typically about 45 mg. Increasing the buffer will usually result in a higher boost of pH inside the oral cavity within a shorter time period.

In one preferred embodiment of the invention, it is preferable that the buffer system materials be chosen so as to yield a pH in excess of at least about 7.5 inside the mouth, and even more desirably in excess of about 8.0, or even greater than about 8.5. A pH level of at least about 9.0 is particularly preferred inside the mouth after about 10 minutes, more preferably after about 5 minutes from the onset of mastication. Even more desirable is a pH of at least about 9.0 after about 3 minutes, and especially after about 1 minute. As heretofore stated, the presence of the buffering system not only seems to facilitate absorption of nicotine inside the mouth, but also seems to facilitate the release of nicotine from certain nicotine ion exchange resins, in particular nicotine polacrilex, as well as from nicotine salts. At the same time, the buffer system is preferably optimized in conjunction with the other components so that it does not result in excessive release of nicotine inside the mouth which would overwhelm the user. The quantity and type of buffer materials furthermore should not cause unpleasant organoleptic side effects, such as irritation, burning, coughing or choking, etc.

Following the initial release of buffer in the first 5–10 minutes or so, there is continued release of buffer at a slower rate. Initial pH of mouth saliva peaks in a range of about 7.5 to 9.5 and thereafter drops back toward basal pH levels as the buffer in the gum is slowly exhausted. As the pH of mouth saliva drops, the fraction of nicotine compound in mouth saliva that is converted to freebase nicotine drops proportionately. The amount of freebase nicotine absorbed during this phase is primarily dependent upon mouth saliva pH. The pleasant, soft chew of the gum composition of the invention encourages additional chewing which facilitates conversion of nicotine compound into freebase nicotine in mouth saliva. This facilitation occurs as a result of increased saliva flow from the stimulation of gum chewing. It is now known that increased saliva flow causes the body to excrete more carbonate buffers into saliva, thereby elevating pH. Thus, the nicotine chewing gum delivery system's buffer component has a second characteristic that serves to compensate for decreasing pH levels which occur after the initial rapid release of nicotine and buffer during the first 5–10 minutes or so. After about 10 minutes or so of chewing, although mouth saliva pH begins to fall because of smaller amounts of buffer release from the gum, there is increased carbonate buffer produced naturally from the stimulation of continued chewing. Consequently, absorption of nicotine continues to be enhanced from increased pH effects caused by the chewing action of the gum.

Thus, the buffer system as part of the present invention provides both a predictable, yet highly effective immediate and an equally efficacious sustained release of the nicotine drug, and absorption thereof. These overall findings appear to be unheralded in the art in their actual physical embodiments. U.S. Pat. No. 3,877,468, for example, calls for the direct acidification of any nicotine delivery system in order to better control the release of the active stimulant. The conventional wisdom appeared to have been that because nicotine was a highly toxic drug, its dosing had to be significantly controlled through acidification.

Also included as part of the nicotine delivery system of the invention may be one or more of non-cariogenic, anti-cavity and tooth whitening ingredients. These are preferably utilized with the non-cariogenic sweeteners heretofore described. U.S. Pat. No. 5,762,911 describes anti-cariogenic agents such as calcium salts, arginine and a cariostatic anion such as an organic phosphate compound. Tooth-whitening compounds include, for example, kaolin, calcium carbonate, silicon dioxide and certain cellulosic materials. These may be include in the final formulation in amounts of from about 0 to 10% by weight, and more preferably from about 0 to 3%.

In a particularly preferred embodiment, the foregoing active nicotine material(s) together with the non-actives, heretofore described, are provided in a substantially non-liquid format. That is, the formulation of the invention is substantially 0% liquid. Typically, chewing gum formulations comprise three major components. These are gum base, solids and liquids. By excluding substantially all liquid from the formulation, incompatibility problems between the various components, and the concomitant problems of instability (especially of the active materials), migration and interaction among the actives, flavors, sweeteners and buffers, etc, can often be avoided.

The combination of active(s), buffer(s) and inert ingredient(s) constituting the nicotine delivery system—chewing gum composition of the invention together result in a formulation which is highly effective as a smoking substitute. The formulation delivers at least about 20%, and more preferably about 25% of its nicotine content after about 5 minutes of chewing. Even more preferably, a further embodiment of the composition can deliver at least about 20%, and more preferably about 25% of its nicotine content after just about 3 minutes or less. It is further within the scope hereof to have the formulation provide the release of at least about 30% or even more of its nicotine content within about 5 minutes, more desirably within about 3 minutes, even more preferably within about 1–2 minutes. In still further embodiments, the amount of nicotine released is up to about 35–40 or even 50% within about 5 minutes, preferably about 3 minutes, or even less such as about 1–2 minutes. In this way, a smoker's physiological need for the drug, which typically lasts about 3–5 minutes, is sated quickly, just as would be accomplished by smoking a cigarette. In particular, during the first 1–2 minutes, the consumer drags more strongly and longer to quickly sate his or her physiological cravings.

The skilled artisan will appreciate from the present disclosure that the foregoing percentages may vary somewhat depending upon the particular source of nicotine utilized, as well as its particular release rate, and the total loading of nicotine included in the final formulation. Thus, for example, a final formulation with a higher total content of nicotine may be formulated with a somewhat lower initial release rate so that the consumer is not overwhelmed.

Preferably, in response to continued chewing, there is continuous, sustained release of nicotine at a rate somewhat lower than that attained during the initial 1–5 minutes or so. Thus, it is within the scope of the invention that about 60% of nicotine content be released within about 10 minutes. It is further within the scope that at least about 80%, more desirably about 90%, and even more preferably about 95% or more of the nicotine content in the chewing gum be released within about 20–30 minutes of mastication. A release of up to about 100% of nicotine content is also contemplated by the invention within about 50 minutes, and preferably about 30 minutes.

Just as importantly, the formulation also provides a continued release of nicotine after the initial mastication period which lasts throughout a chewing period of about 20 minutes on up to about 30 minutes or so. The release of nicotine is substantially independent of the actual chew rate in the sense that active release will occur whether the composition is chewed continuously, or whether the "park and chew" method is utilized. Thus, the consumer does not have to be particularly conscious of his/her chewing action in order to effectively receive nicotine. However, at the same time, if chewers feel a continuing need for nicotine after a number of minutes, they can chew more rapidly, whereas if they feel their cravings subsiding, they can chew more slowly, and thereby release less nicotine. Consequently, the product of the invention is still responsive to the needs of the chewer, who can adjust intake of nicotine to match their cravings.

The recovering smoker can thereby be assured that the product in its various embodiments will keep delivering a steady stream of nicotine, even after several minutes of chewing. In contrast to the present invention, many existing products seek to provide a constant release rate throughout the entire period of chewing. This results in a relatively small amount of nicotine being released initially over the first critical 10 minutes of chewing. During this time the smoker could be experiencing severe craving and/or symptoms of withdrawal which would prompt him or her to return to smoking. In contrast, the various embodiments of the present invention provide an initial burst of nicotine over the first 10 minutes to satisfy immediate cravings. A continued release thereafter helps to keep the recovering smoker sated over time. The invention achieves its objectives without causing irritation inside the mouth, upset stomach or other discomfort to the user.

The various embodiments of the nicotine delivery system—chewing gum composition heretofore described may be formulated into any desired shape or size. Preferably, the composition will take the shape of sticks or tabs, or any other form which is typically utilized by chewing gum manufacturers. The various formulations herein described are prepared using methods known in the confectionery industry for preparing commercial chewing gums. For example, the gum base is first softened by elevating its temperature, and adding softeners thereto by mixing. Next, any solid material (such as sweeteners in solid form) is combined therein by mixing. Finally, the active nicotine and any optional liquid material is also added by mixing. The composition is allowed to set and is shaped into serving sizes, which may be within the range of about 0.5 to 5.0 grams, preferably about 1–2 grams. In addition, each serving may be coated with an edible confectionery-type shell, with or without any active nicotine ingredient.

In another embodiment of the invention, there is provided a chewing gum delivery system in which a gum base matrix material in the form of granulates has one or more of the active nicotine substances interspersed among the granulates. The gum base granulates together with the active(s) are compressed together to yield the final formulation. The gum base matrix may be material as heretofore described, i.e. that which facilitates release of the active (as for example that having a hydrophilic moiety, or a butyl rubber-based moiety), or may be other gum matrix material known in the art. For example, a low moisture, non-aqueous gum base matrix having a high degree of hydrophobicity may be utilized in certain formulations. In certain situations, the gum base matrix material and the nicotine can have different, somewhat incompatible moieties so that the nicotine is not strongly retained by the gum base matrix, and can be released more easily.

In this embodiment of the invention wherein gum base granulates are used, it is especially desirable that the nicotine be thoroughly dispersed among the gum base granulate matrix, but preferably not be contained within the granulates themselves. It may also be desirable that the nicotine substantially enrobe or surround each of the individual granulates as well.

To therefore prepare this embodiment of the nicotine chewing gum composition of the invention, the procedures set forth in U.S. Pat. No. 4,405,647 may be especially helpful to the skilled artisan. Briefly stated, the gum base material may be melted or softened using one or more of the softening agents, plasticizers and/or solvent and filler materials heretofore described. The sweeteners and flavors, whether processed via flash-flow processing or other traditional mixing methods, are then admixed into the gum base. This is accomplished by comminuting the gum base material together with the water-soluble ingredients in a bed or blender within a gaseous medium at room temperature, as described in the aforementioned U.S. Pat. No. 4,405,647. This material is continuously pulverized and thereby chopped into much smaller particles. To prevent adherence of the resultant particles to one another, additional filler or bulking material may be added like lubricants, glidants and other tableting and compression aids well known in the pharmaceutical industry, such as for example, silica gel or calcium carbonate. Granules of any desired size and shape may be obtained upon the introduction of a standard mess screen to separate the particulates once formed.

The next step in forming the final chewing gum composition involves adding the nicotine active to the formed particulates. This is done by admixing the nicotine, whether in free form or encapsulated as heretofore described, with the pulverized materials so as to substantially disperse the nicotine among the particulates. In a preferred mode, the nicotine may be added along with the tableting, lubrication or other compression aids. The active material thus becomes substantially entrapped in the multitude of spaces between the individual gum particles. Upon thorough mixing by any suitable device, the materials are then compressed and compacted in a tablet press or other suitable device. In this way the nicotine is sandwiched in the voids in between the compressed particulate gum granulate material. The active substance is thoroughly dispersed between and throughout the resulting matrix. The active is thus "external" to the gum base material itself. The result is an external delivery system for nicotine. In a particularly preferred embodiment, the active material(s) together with the non-actives, heretofore described, are provided in a substantially non-liquid format. That is, the formulation of the invention according to this embodiment is preferably substantially 0% liquid.

Other possible physical embodiments of the nicotine chewing gum composition of the invention include, for example, various centerfill configurations. In these embodiments the gum base matrix will at least partially surround a centerfill. The centerfill will contain one or more of the active nicotine substances. The centerfill may be a liquid or semi-liquid material and preferably will be low fat or fat free. In addition to the active(s), the centerfill may contain one or more sweeteners and/or flavorants as heretofore described. A combination of saccharide material, flavoring, polyol and edible gel material is one example of a centerfill. One or more of the active ingredient(s) and/or the sweeteners and flavorants, etc. may be encapsulated as previously set forth, and then incorporated into the centerfill.

The centerfill embodiments may be prepared using methods known in the confectionery and chewing gum industries. For example, U.S. Pat. No. 3,806,290 describes a method for forming centerfill chewing gum by extruding a hollow-centered rope of chewing gum through an orifice having a pair of concentric conduits extending therethrough. A centerfill material is fed through the inner conduit to the hollow center upstream through a space between the inner and outer conduits. The centerfill rope of chewing gum is passed to a sizing unit having a plurality of pairs of rollers for progressively decreasing a cross-sectional dimension of the gum rope. The plurality of pairs of rollers includes at least one vertical pair of rollers having vertically aligned axes of rotation and overlapping lower flange portions. Ramp means are provided for guiding the gum rope above the roller flange portions upon entry of the gum rope between the vertical pair of rollers. Other methods of forming centerfill chewing gum known in the art may also be utilized.

The centerfill embodiment may be particularly desirable wherein immediate release of the nicotine active is particularly desired. Encapsulating the active ingredient(s) in this embodiment may help to taste-mask those actives which provide an undesirable organoleptic sensation. Other than the centerfill portion, it is preferred that the formulation ingredients of this embodiment also be substantially liquid-free, or about 0% liquid.

A further embodiment will include a gum base matrix containing nicotine, together with a centerfill containing nicotine as well. The nicotine in the centerfill can be released quickly to satisfy cravings, while the matrix can release nicotine over time thereafter to maintain nicotine levels in the blood.

The nicotine delivery system of the invention can be used for a variety of therapeutic purposes including: 1) the relief of craving and withdrawal symptoms during situational abstinence (e.g., on a plane, smoke-free offices, etc.); 2) as part of a smoking reduction program; and 3) as part of a smoking cessation program. After introduction of a serving size piece of the gum composition into the mouth, the consumer will chew the gum as is normally done with any non-medicated type of chewing gum for about 20–30 minutes, but at approximately an average rate of about 10–20 chews per minute. The gum is then discarded. This process is repeated as long as nicotine cravings arise or the risk of smoking is present. Care should be exercised, however, to avoid overdosing on this smoking substitute. A serving of the nicotine chewing gum delivery system of the invention is designed to cause a loaded nicotine concentration level in the bloodstream of at least about 2 to 7 nanograms of nicotine per milliliter of blood. More preferably, at least about 3 ng/mL nicotine will be attained, and more preferably at least about 5 ng/mL. If desired, the present invention can attain a nicotine concentration of 10 ng/mL. in the bloodstream. Preferably, nicotine blood levels will be elevated after about 3–5 minutes of chewing. Desirably, the foregoing levels can be maintained for at least about 30 minutes, and preferably about 45–60 minutes after the onset of chewing.

While the invention has been described with particular reference to smoking reduction or cessation, it is also within the scope hereof that the nicotine delivery system heretofore described also be utilized in the treatment of certain diseases as well. For example, recent studies have demonstrated that nicotine therapy can be particularly beneficial to persons with ulcerative colitis, Parkinson's disease, Tourette's syndrome and Alzheimer's disease as well.

The following examples illustrate various preferred embodiments of the invention, but are not to be construed as limiting the scope thereof:

EXAMPLES

Examples of the delivery system were prepared in gum form and tested for effectiveness and performance of nicotine delivery. Three different gum bases served as ingredients for the examples. GUM BASE X included butyl rubber in an amount by weight of about 5.0%, polyisobutylene in an amount by weight of about 9.0%, rosins in an amount by weight of about 10%, polyvinyl acetate in an amount by weight of about 24%, plasticizer in an amount by weight of about 20%, emulsifier in an amount by weight of about 6.5%, microcrystalline wax in an amount by weight of about 5.0%, and dicalcium phosphate in an amount by weight of about 20.5%. GUM BASE Y, by contrast, included mono & diglycerides E471 in a form commercialized under the trademark MYVAPLEX 600 and in an amount by weight of about 40%, mono & diglycerides in a form commercialized under the trademark DUREM 117 and in an amount by weight of about 40%, soy lecithin in a form commercialized under the trademark CENTROL 3F UB and in an amount be weight of about 19.9%, and dicalcium phosphate anhydrous FCC in an amount by weight corresponding to about 0.1%.

GUM BASE Z included polyvinyl acetate in an amount by weight of about 38%, rosin in an amount by weight of about 10%, partially hydrogenated soybean oil in an amount by weight of about 11%, polyisobutylene in an amount by weight of about 12%, dicalcium phosphate in an amount by weight of about 13.92%, triacetin in an amount by weight of about 3%, mono-di-glycerides in an amount by weight of about 7%, microcrystalline wax in an amount by weight of about 5%, and BHT in an amount by weight of about 0.08%.

The nicotine in some of the following examples can be provided in encapsulated form. An exemplary encapsulation form, referred to hereinafter as "ENCAPSULATION FORM I" includes nicotine hydrogen tartrate USP in an amount by weight of about 13.51%, MANNITOL 35 in an amount by weight of about 28.83%, and Sorbitol (NEOSORB P 60 W) in an amount by weight of about 57.66%. Another exemplary encapsulation form, referred to hereinafter as "ENCAPSULATION FORM II" includes nicotine hydrogen tartrate USP in an amount by weight of about 12.98%, Sorbitol in an amount by weight of about 43.02%, Mannitol 35 in an amount by weight of about 29%, and MYVAPLEX 600P (mono & diglyceride, 90%) in an amount by weight of about 15%. Yet another exemplary encapsulation form, referred to hereinafter as "ENCAPSULATION FORM III" includes nicotine hydrogen tartrate salt USP in an amount by weight of about 14.57% and Sorbitol in an amount by weight of about 85.43%.

In the following examples, the nicotine delivery system of the invention was compared to certain control formulations, as well as the commercial formulation available under the trademark Nicorette®. Comparisons were made in the ability of the delivery systems to release nicotine and also control the pH of saliva in the mouth, thereby resulting in effective absorption of nicotine into the bloodstream. Release of nicotine from the delivery system was measured by analysis of the remaining nicotine in the delivery system at timed intervals following human subjects chewing gum samples. The pH of saliva was measured during chewing by collection of saliva samples. For each "chew out" study, the following protocol was observed: A serving size of gum (approximately 1.0 gram each) was chewed at a timed rate of 15 chews per minute by human subjects for different chewing intervals up to a total period of 30 minutes. Each serving of gum contained approximately 2 mg. of nicotine. At the intervals noted on the graphs corresponding to the Examples, the amount of residual nicotine remaining in the gum was measured to determine the percentage released within that time period. Nicotine measurements were made by High Performance Liquid Chromatography (HPLC).

Calibration curves were constructed with standard nicotine solutions. The amount of nicotine released was determined by subtraction of the residual amount of nicotine from the starting amount. Saliva pH measurements were made utilizing a calibrated pH meter. In addition, blood specimens were collected from subjects during chewing and nicotine concentrations were measured by gas chromatography-mass spectrometry (GC-MS). Deuterated nicotine was used as the internal standard and standard nicotine calibration solutions were processed along with the specimens. The limit of quantitation of the GC-MS assay was 1-ng/mL.

Example 1

In this example, chew out studies were conducted with five human subjects using Formula A according to one embodiment of the invention, and 2 mg NICORETTE gum. Formula A contained nicotine hydrogen tartrate (approximately 2.2 mg of nicotine base). In addition, the delivery system of Formula A was buffered with 45 mg of potassium carbonate. More specifically, Formula A included GUM BASE X in an amount by weight of about 55%, GUM BASE Y in an amount by weight of about 4.5%, nicotine in ENCAPSULATION FORM I in an amount by weight of about 5%, Sorbitol (NEOSROB P 60 W) in an amount by weight of about 28%, potassium carbonate USP (extra fine) in an amount by weight of about 4.5%, mint flavor in an amount by weight of about 2.4%, and AF menthol in an amount by weight of about 0.6%. In addition, talc USP (e.g,. MP98-30) was added as a processing aid in an amount by weight substantially equal to the amount of menthol.

The percentage of nicotine released is shown in FIG. 1A. As can be seen from FIG. 1A, the NICORETTE formulation released its nicotine quite slowly over the entire 30 minute period. Formula A, on the other hand, provided a rapid release of nicotine within the first 3–10 minutes, followed by continued slower release thereafter, resulting in overall greater release of nicotine compared to 2 mg Nicorette.

In FIG. 1B, the release rate (mg nicotine released/minute) over time is illustrated for Formula A compared to 2 mg Nicorette. The amount of nicotine released from the gum is plotted versus the mid-point of each chewing interval. The early rapid release of nicotine by Formula A was three times faster over the first 3 minutes of chewing compared to 2 mg Nicorette. Following a very fast initial rate of 0.12 mg/minute over the first 3 minutes, Formula A released at an average rate of 0.07 mg/minute over the remaining period of mastication. In the case of 2 mg Nicorette, the release rate was nearly constant throughout the entire mastication period ranging from 0.03 mg/minute to 0.06 mg/minute. The maximum rate of nicotine released by Formula A (0.12 mg/minute) was two-fold greater than the maximum release rate of Nicorette (0.06 mg/minute).

Example 2

In this example, chew out studies were conducted with five human subjects using Formula B according to another embodiment of the invention and compared to 2 mg NICORETTE gum. Formula B contained nicotine polacrilex (approximately 2 mg of nicotine base). More specifically, Formula B included GUM BASE X in an amount by weight of about 55%, sorbitol NEOSORB P 60 W in an amount by weight of about 22.27%, xylitol CM 90 in an amount by weight of about 16%, a flavoring substance in an amount by weight of about 2.5%, nicotine polacrilex in an amount by weight of about 1.23%, potassium carbonate in an amount by weight of about 2%, and potassium bicarbonate in an amount by weight of about 1%.

Each serving of the delivery system of Formula B was buffered with a combination of 20 mg of potassium carbonate and 10 mg of potassium bicarbonate. As can be seen from FIG. 2, the NICORETTE formulation released its nicotine quite slowly over the entire 30 minute period. Formula B, on the other hand, provided a rapid release of nicotine within the first 3–10 minutes, followed by continued slower release thereafter, resulting in slightly greater release of nicotine compared to 2 mg Nicorette. Formula B was also more effective in early release of nicotine over the first 10 minutes of chewing compared to 2 mg NICORETTE. Thus, this formulation containing the same nicotine moiety (nicotine polacrilex) and content as 2 mg NICORETTE released substantially more nicotine at a faster rate over the entire chewing period as a result of the improved properties of the gum base.

Example 3

In this example, the pH of saliva during chewing was measured during the chew out period (20 chews/minute) for five formulations, namely, Formula C, Formula D, Formula E, Formula F, and Formula G. Formula C included GUM BASE X in an amount by weight of about 55%, Sorbitol (NEOSORB P 60 W) in an amount by weight of about 17%, Xylitol milled USP VCC in an amount by weight of about 16%, a buffering system of potassium carbonate USP (extra fine) in an amount by weight of about 4.5%, nicotine in hydrophilic ENCAPSULATION FORM III in an amount by weight of about 5%, and cooling mint flavor in an amount by weight of about 2.5%.

Formulas C, D, E, and F were identical, except that the buffering systems consisted of the following: Formula C, 45 mg of potassium carbonate (4.5% by weight); Formula D, 30 mg of potassium carbonate (3.0% by weight) and 15 mg of potassium bicarbonate (1.5% by weight); Formula E, 15 mg of potassium carbonate (1.5% by weight) and 30 mg of potassium bicarbonate (3.0% by weight); and Formula F, 45 mg of potassium bicarbonate (4.5% by weight).

Formula G was unbuffered and included GUM BASE X in an amount by weight of about 55%, Sorbitol in an amount by weight of about 25.31%, Xylitol in an amount by weight of about 16%, mint flavor in an amount by weight of about 3%, and nicotine hydrogen tartrate in an amount by weight of about 0.69%.

The results are set forth in FIG. 3. As can be seen, the pH of saliva during chewing was progressively increased with increasing proportions of potassium carbonate. This demonstrates that a buffering system as part of a nicotine delivery system greatly facilitates a higher pH environment inside the mouth. Such a buffering system can be adjusted to deliver a desirable amount of buffer. This, in turn, further facilitates the absorption of a pH dependent compound such as nicotine.

Example 4

For this example, salivary pHs (mean data for 5 subjects) during chewing of Formulas A and G (unbuffered) were compared, as shown in FIG. 4, with salivary pHs of 2 mg NICORETTE gum chewed at the same rate (15 chews/minute) by the same subjects.

During chewing of Formula A, the pH of saliva increased within the first 1 minute to a maximum pH of 9.05 and was followed by a decline to approximately 8.30 at 5 minutes and an even slower decline to normal levels over the remaining 20 minutes. In contrast, the pH of saliva during chewing of 2 mg Nicorette increased slowly to a maximum of approximately 7.88 at 5 minutes followed by a very slow decline over the remaining time. Formula G illustrates the small changes in pH that occur naturally by the stimulating action of chewing upon salivary contents. This demonstrates that the buffering system of Formula A is releasing buffer rapidly in the early stages of chewing at the appropriate time to greatly facilitate the absorption of nicotine.

Example 5

As shown in FIG. 5, this example illustrates mean plasma data from four subjects who chewed Formula A and 2 mg Nicorette. During chewing, blood specimens were collected, centrifuged and plasma separated for analysis by GC-MS. Starting baseline levels (zero time) were subtracted from measured nicotine concentrations at each time of collection. Release of nicotine from Formula A gum resulted in a rapid increase in blood levels over the first 10 minutes of chewing compared to 2 mg Nicorette gum. Nicotine levels continued to increase over the 30 minute chewing period for both gums. The early rapid release of nicotine by the Formula A gum resulted in a nicotine blood level difference of approximately 3 ng/mL at 10 minutes. Continued release of nicotine by the Formula A gum ultimately produced a difference of approximately 4 ng/mL at 30 minutes. This demonstrates the effectiveness of the Formula A gum in providing early and sustained release of nicotine into the oral cavity followed by effective absorption into the bloodstream across the oral mucosa as a result of buffer control of saliva pH conditions.

Example 6

For this example, the effect of softening agents was observed on the nicotine release rate. Formulas C, H, and A included the exemplary GUM BASE X, which is butyl-rubber-based, together with nicotine hydrogen tartrate as the active. The buffering system was provided in the form of 45 mg. of $K_2CO_3$ per serving. Formula H included GUM BASE X in an amount by weight of about 55%, GUM BASE Y in an amount by weight of about 2.3%, Sorbitol (NEOSORB P 60 W) in an amount by weight of about 30.2%, mint flavor in an amount by weight of about 2.4%, a buffering system consisting of potassium carbonate USP (extra fine) in an amount by weight of about 4.5%, AF menthol in an amount by weight of about 0.6%, and nicotine in ENCAPSULATION FORM II in an amount by weight of about 5.0%. Formula H also included some talc USP MP98-30 as a processing aid in an amount by weight equal to the menthol.

Formulas A and H included softening plasticizers (e.g., MYVAPLEX 600, DUREM 117, and the like) according to preferred embodiments of the invention. Formulation C did not contain any such softening plasticizers. Loading of softening plasticizer was 1/3 higher in Formulation A than in H. As illustrated in FIG. 6, Formulations A and H both facilitated a higher nicotine release rate within about 10 minutes than did Formulation C.

The foregoing examples demonstrate how changes in the formulation of the gum base and/or changes in the buffering system can be used to modify how the nicotine (or actives that behave like nicotine) is delivered. While the foregoing examples include the butyl-rubber-based GUM BASE X, it is understood that the invention is not limited to the exemplary embodiments. Non-butyl-rubber-based gums, for example, can be used to implement alternative embodiments of the present invention.

Example 7

In this example, a chew out study was conducted using Formula J, and compared to Nicorette gum. Formula J contained 60% gum base matrix, of which approximately 35–40% was PVA polymer material (with no butyl rubber), along with 100% nicotine polacrilex as the nicotine active. The delivery system of Formula J was buffered using a combination of sodium carbonate and sodium bicarbonate in about a 2:1 weight ratio. Each serving of the delivery system included 20 mg. of the sodium carbonate and 10 mg of the sodium bicarbonate. More specifically, Formula J included GUM BASE Z in an amount by weight of about 60%, sorbitol in an amount by weight of about 17.27%, xylitol in an amount by weight of about 16%, sodium carbonate in an amount by weight of about 2%, sodium bicarbonate in an amount by weight of about 1%, nicotine polacrilex in an amount by weight of about 1.23%, and flavor in an amount by weight of about 2.5%.

The same participant chewed each gum separately over time at a rate of 10 chews/minute. The percentage of nicotine released is shown in FIG. 7. As can be seen from FIG. 7, the Nicorette formulation released its nicotine quite slowly over the entire 30 minute period. Formula J, on the other hand, provided an excellent release of nicotine within the first 3–5 minutes, and a steady release hereafter.

Example 8

For this example, another chew-out study was conducted using a different participant. Formula J was again utilized, as was Nicorette gum. Formula K also was tested. Formula K was substantially identical to Formula J, except that 100% nicotine salt (nicotine tartrate) served as the nicotine active. More specifically, Formula K included GUM BASE Z in an amount by weight of about 60%, sorbitol in an amount by weight of about 17.81%, xylitol in an amount by weight of about 16%, sodium carbonate in an amount by weight of about 2%, sodium bicarbonate in an amount by weight of about 1%, nicotine hydrogen tartrate in an amount by weight of about 0.69%, and flavor in an amount by weight of about 2.5%.

Figure 8:
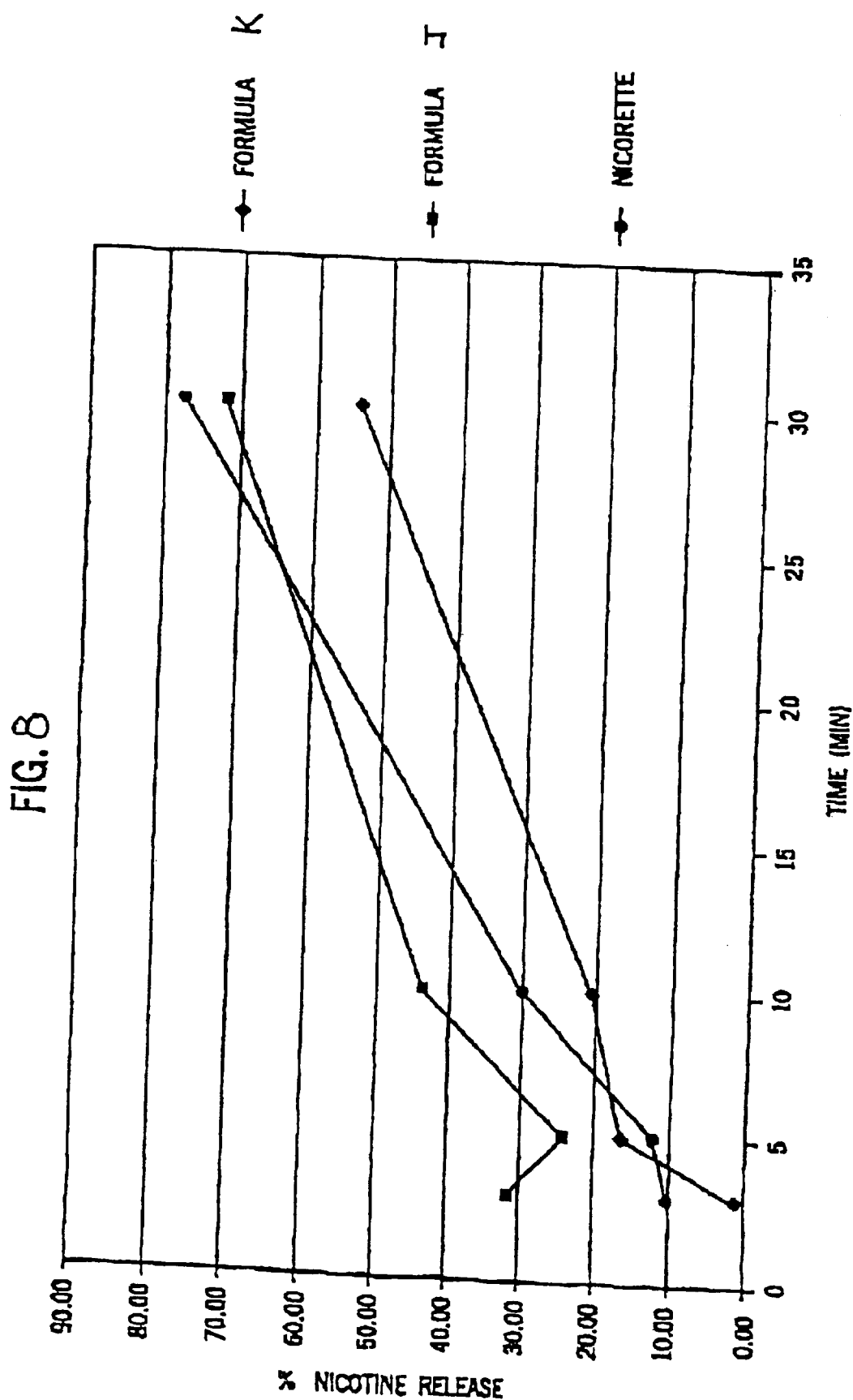
FIG. 8 is a graph comparing cumulative nicotine release profiles of the first exemplary non-butyl rubber-based embodiment of the present invention, a second exemplary non-butyl rubber-based embodiment of the present invention, and the commercially available nicotine gum.

The chew rate was 20 chews/minute over the course of 30 minutes total. The results are shown in FIG. 8. Again, Formula J of the invention had an excellent release rate of nicotine. The release rate of Formula K was not quite as fast as that of Formula J.

Example 9

In this example, the pH generated as a result of chewing was measured during the chew out period (20 chews/minute) for three formulations, namely, Formula J, Nicorette, and Formula L. Formula L was identical to Formula J, except that it contained 55% gum base matrix and the buffering system was a combination of potassium carbonate and potassium bicarbonate. More specifically, Formula L included GUM BASE Z in an amount by weight of about 55%, sorbitol in an amount by weight of about 17.27%, xylitol in an amount by weight of about 16%, potassium carbonate in an amount by weight of about 2%, potassium bicarbonate in an amount by weight of about 1%, nicotine polacrilex in an amount by weight of about 1.23%, and flavor in an amount by weight of about 2.5%.

Figure 9:
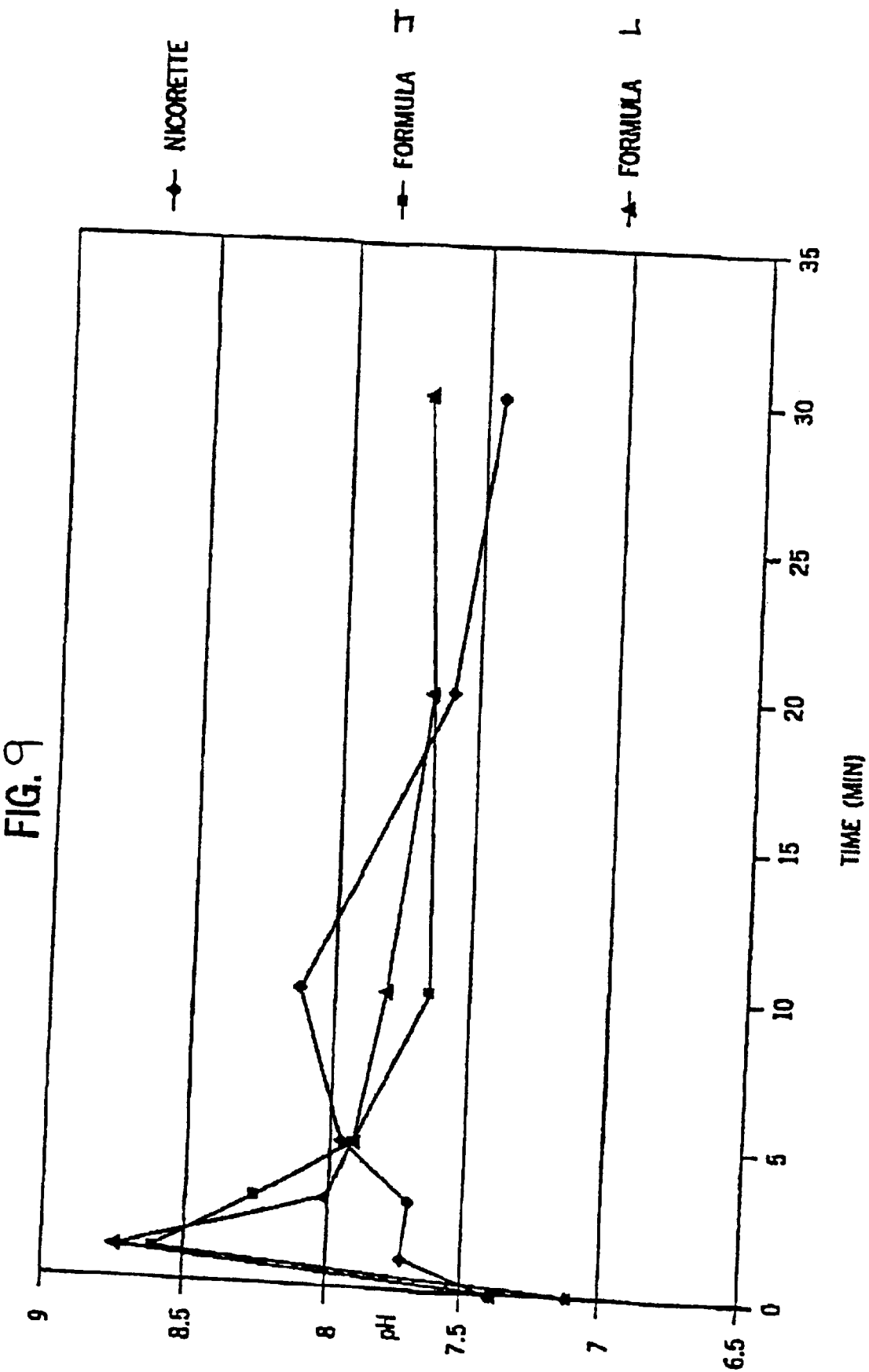
FIG. 9 is a graph comparing salivary pH achieved over time in response to separate chewing of the first exemplary non-butyl rubber-based embodiment of the present invention, a third exemplary non-butyl rubber-based embodiment of the present invention, and the commercially available nicotine gum.

The results are set forth in FIG. 9. As can be seen, the pH obtained with Formulas J and L were considerably higher than was the pH obtained with the Nicorette formulation. This demonstrates that a buffering system as part of a nicotine delivery system greatly facilitates a higher pH environment inside the mouth. This, in turn, further facilitates the absorption of a pH-dependent compound such as nicotine. Notably, the rise in pH occurred early in the chewing process.

The invention also provides that the buffering system heretofore described may be utilized with any type of confectionery formulation in which a controlled release under proper pH, and preferably alkaline pH conditions, is warranted.

The foregoing exemplary embodiments provide a convenient, reliable, practical, and relatively painless system for delivering an active. They are capable of delivering initial and second doses of a craving reduction active or other actives (a bi-phasic delivery), the combination of which rapidly reduces cravings, or provides some other pharmacological effect, and provides the pharmacological effect or protection from such cravings over a prolonged period of time beyond the initial dose. Notably, the delivery system of the present invention is capable of rapidly achieving a pharmacologically effective concentration of the active (e.g., nicotine) in the bloodstream (e.g., within 5 minutes, or more desirably within 3 minutes, or in some cases, within 1–2 minutes), and is also capable of keeping the concentration of the active in the bloodstream at or near the pharmacologically effective concentration for at least 20 minutes after chewing of the delivery system begins, or more desirably about 30 minutes to about 50 minutes after chewing begins.

While the foregoing examples contain only one form of the active (e.g., nicotine hydrogen tartrate or nicotine polacrilex) for both the initial and second doses of the active, it is understood that the active can be provided in more than one form. The initial dosage, for example, can be delivered using one form of the active, and the second dosage can be provided by another form of the active.

Similarly, the exemplary dosage amount of about 2 milligrams is not a limitation of the present invention. It will be appreciated from the foregoing teachings that alternative dosage amounts can be provided (e.g., 1–10 milligrams of nicotine, or more desirably, 1–4 milligrams) by suitably modifying the composition that defines the delivery system, especially if the active is not nicotine.

It is expected that certain changes or modifications to the invention herein described may be effected by those skilled in the art without departing from the true spirit and scope thereof as set forth in the claims and the accompanying specification.

What is claimed is:

1. A chewing gum composition for systemic, oral administration of a nicotine constituent, said composition comprising:
    a) a nicotine constituent;
    b) a gum base matrix, said gum base matrix including at least one substantially hydrophilic polymer and at least one hydrophobic polymer; and
    c) a buffer, whereby said nicotine constituent is administered by the chewing gum composition in a bi-phasic manner.

2. The composition of claim 1, wherein said composition provides for at least about 25% release of nicotine content within about 5 minutes after the onset of chewing.

3. The composition of claim 2, wherein said composition provides for at least about 25% release of nicotine within about 3 minutes after the onset of chewing.

4. The composition of claim 2, wherein said nicotine is in the form of at least one member selected from the group consisting of nicotine polacrilex and the pharmaceutically acceptable salts of nicotine.

5. The composition of claim 4, wherein said nicotine comprises at least one member selected from the group consisting of nicotine hydrogen tartrate and nicotine bitartrate.

6. The composition of claim 1, wherein said gum base matrix comprises polyvinylacetate as said hydrophilic polymer and at least one hydrophobic polymer member selected from the group consisting of water-insoluble, natural and synthetic elastomers, polymers and rubbers.

7. The composition of claim 6, wherein said hydrophobic polymer member is at least one member selected from the group consisting of butadiene-styrene copolymers, butyl rubber, polyethylene, polyisobutylene and polyvinylesters.

8. The composition of claim 7, wherein said gum base matrix comprises polyvinylacetate, as said hydrophilic polymer, said polyvinylacetate having a molecular weight within the range of about 12,000 to about 45,000.

9. The composition of claim 8, wherein said nicotine is nicotine polacrilex.

10. The composition of claim 8, wherein said gum base matrix comprises butyl rubber and polyisobutylene, as said hydrophobic polymer and wherein said polyvinylacetate has a molecular weight of about 12,000, said gum base matrix comprising less than about 70% of said composition.

11. The composition of claim 10, wherein said polymers comprise about 25–75% of said gum base matrix.

12. The composition of claim 11, wherein said polymers comprise about 50–60% of said gum base matrix, and said gum base matrix comprises about 50–60% of said composition.

13. The composition of claim 12, wherein said nicotine is at least one member selected from the group consisting of nicotine hydrogen tartrate and nicotine bitartrate.

14. The composition of claim 13, further comprising at least one bulk sweetener selected from the group consisting of mono-, di-, tri- and polysaccharides, and natural and synthetic non-saccharide-based sweeteners.

15. The composition of claim 14, wherein said bulk sweetener is at least one member selected from the group consisting of sorbitol and xylitol.

16. The composition of claim 12, wherein said buffer is at least one member selected from the group consisting of potassium carbonate, potassium bicarbonate, sodium carbonate and sodium bicarbonate.

17. The composition of claim 16, further comprising at least one filler material which facilitates release and/or absorption of nicotine.

18. The composition of claim 1, wherein said buffer comprises at least one buffer material which is at least one member selected from the group consisting of sodium carbonate, sodium bicarbonate, potassium carbonate, potassium bicarbonate, dipotassium phosphate, and potassium citrate, and wherein said buffer raises the pH inside the mouth to at least about 7.5 within about 5 minutes of chewing said composition.

19. The composition of claim 18, wherein said composition is substantially liquid-free.

20. The composition of claim 1, wherein said gum base matrix and said buffer are configured to rapidly achieve a pharmacologically effective concentration of nicotine in the bloodstream within about 5 minutes after chewing of the composition begins and also to keep the concentration of nicotine in the bloodstream at or near the pharmacologically effective concentration for at least 20 minutes after chewing begins.

21. The composition of claim 20, wherein said gum base matrix and said buffer are configured to rapidly achieve said pharmacologically effective concentration of nicotine in the bloodstream within about 3 minutes after chewing begins.

* * * * *